(12) United States Patent
Yuan

(10) Patent No.: US 8,404,736 B2
(45) Date of Patent: Mar. 26, 2013

(54) HETEROCYCLIC AMIDE DERIVATIVES AS EP4 RECEPTOR ANTAGONISTS

(75) Inventor: Wei Yuan, Fishers, IN (US)

(73) Assignee: Beta Pharma Canada Inc., Montreal, Quebec (CA)

( * ) Notice: Subject to any disclaimer, the term of this patent is extended or adjusted under 35 U.S.C. 154(b) by 0 days.

(21) Appl. No.: 13/058,384

(22) PCT Filed: Aug. 13, 2009

(86) PCT No.: PCT/US2009/053748
§ 371 (c)(1),
(2), (4) Date: Feb. 10, 2011

(87) PCT Pub. No.: WO2010/019796
PCT Pub. Date: Feb. 18, 2010

(65) Prior Publication Data
US 2011/0136887 A1 Jun. 9, 2011

Related U.S. Application Data

(60) Provisional application No. 61/188,888, filed on Aug. 14, 2008.

(51) Int. Cl.
*A61K 31/407* (2006.01)
*C07D 495/02* (2006.01)
(52) U.S. Cl. .................. 514/412; 548/452; 548/453
(58) Field of Classification Search ............ 548/452, 548/453; 514/412
See application file for complete search history.

(56) References Cited

U.S. PATENT DOCUMENTS 7,705,035 B2 * 4/2010 Boyd et al. .................. 514/415
7,968,578 B2 * 6/2011 Boyd et al. .................. 514/373

FOREIGN PATENT DOCUMENTS

| WO | WO 2007/121578 | 11/2007 |
| WO | WO 2007/143825 | 12/2007 |
| WO | WO 2008/104055 | 9/2008 |
| WO | WO 2009/005076 | 1/2009 |

OTHER PUBLICATIONS

Boyd et al (2007): STN International HCAPLUS database, Columbus (OH), accession No. 2007: 1237193.*
Nozawa et al (2009): STN International HCAPLUS database, Columbus (OH), accession No. 2009: 20265.*
The International Search Report and Written Opinion of the International Searching Authority for PCT/US09/53748, date completed Oct. 19, 2009, date mailed Oct. 29, 2009.
The Supplementary European Search Report for EP 09807305.9, dated Apr. 5, 2012.

* cited by examiner

*Primary Examiner* — Golam M M Shameem
(74) *Attorney, Agent, or Firm* — Miller Canfield Paddock and Stone; Weisun Rao

(57) ABSTRACT

The invention relates to compounds of Formula (I) (or pharmaceutically acceptable salts thereof) as defined herein, pharmaceutical compositions thereof, and their use in manufactures and methods for modulating biological processes including antagonism of Prostaglandin EP4 receptor as a therapeutic treatment.

14 Claims, No Drawings

HETEROCYCLIC AMIDE DERIVATIVES AS EP4 RECEPTOR ANTAGONISTS

CROSS REFERENCE TO RELATED APPLICATIONS

This application is a national phase application and claims the benefit, under 35 U.S.C. §371, of PCT/US2009/053748, filed on Aug. 13, 2009, which in turn claims the priority of U.S. Application No. 61/188,888, filed on Aug. 14, 2008. All applications are incorporated herein by reference in their entireties.

BACKGROUND OF THE INVENTION

This invention relates to heterocyclic amide derivatives, or their pharmaceutically acceptable salts, pharmaceutically acceptable prodrugs, pharmaceutical compositions made therefrom, and their medical use in mammals including humans. The compounds of this invention have activity as prostaglandin E2 receptor antagonists, which are useful in the treatment or alleviation of pain and inflammation, as well as other inflammation-associated disorders such as arthritis.

Prostaglandins are mediators of pain, fever and other symptoms associated with inflammation. Prostaglandin E2 (PGE2) is the predominant eicosanoid associated with inflammation. In addition, PGE2 is also involved in various physiological and/or pathological conditions such as hyperalgesia, uterine contraction, digestive peristalsis, awakeness, suppression of gastric acid secretion, blood pressure, platelet function, bone metabolism, angiogenesis and the like. Four PGE2 receptor subtypes (EP1, EP 2, EP3 and EP4) displaying different pharmacological properties have been identified and cloned. The EP4 subtype, a Gs-coupled receptor, stimulates cAMP production, and is distributed in a wide variety of tissue types suggesting a major role in PGE2-mediated biological events. Patent publications WO 96/06822, WO 96/11902, EP 752421-A1, WO3/16254, WO5/021508, and WO7/121578 disclose various compounds for the treatment of prostaglandin mediated diseases.

The characterization and therapeutic relevance of the prostanoid receptors and their most commonly used selective agonists and antagonists have been investigated: Eicosanoids: From Biotechnology to Therapeutic Applications, Folco, Samuelsson, Maclouf, and Veto eds, Plenum Press, New York, 1996, chap. 14, 137-154; Journal of Lipid Mediators and Cell Signalling, 1996, 14, 83-87; and Prostaglandins and Other Lipid Mediators, 2002, 69, 557-573.

Thus, selective prostaglandin ligands, agonists or antagonists, depending on which prostaglandin E receptor subtype is being considered, have anti-inflammatory, antipyretic and analgesic properties similar to a conventional non-steroidal anti-inflammatory drug. In addition, selective prostaglandin ligands have effects on vascular homeostasis, reproduction, gastrointestinal functions and bone metabolism. Unlike NSAIDs, which are indiscriminate cyclooxygenase inhibitors, selective prostaglandin ligands may have reduced side effects. In particular, such compounds are believed to have reduced potential for gastrointestinal toxicity, reduced potential for renal side effects, reduced effect on bleeding times, and reduced induction of asthma attacks in aspirin-sensitive subjects.

Studies have shown that chronic inflammation induced by collagen antibody injection in mice is mediated primarily through the EP4 subtype of PGE2 receptors. See e.g. *Journal of Clinical Investigation* (2002, 110, 651-658). More recently, in *Nature Medicine* (Yao et. al. published online 24 May 2009), studies provided evidences that showed PGE2-EP4 signaling promotes immune inflammation through TH1 differentiation and TH17 expansion, thus suggesting that EP4 antagonism may be therapeutically useful for immune diseases such as multiple sclerosis, rheumatoid arthritis, inflammatory bowel diseases, and allergic skin disorders.

The present invention relates to novel compounds and methods for treating prostaglandin E2 mediated diseases, and pharmaceutical compositions thereof. The compounds of the invention are structurally different from NSAIDs and opiates, and are antagonists of the pain and inflammatory effects of E-type prostaglandins. In particular, the present invention relates to novel compounds that are antagonists of the EP4 subtype of PGE2 receptors. The compounds are therefore expected to be useful in mammals including humans for the treatment of diseases or conditions mediated by the EP4 receptor, including acute and chronic pain, osteoarthritis, rheumatoid arthritis and cancer.

SUMMARY OF THE INVENTION

The invention relates in one aspect to a series of novel amide derivatives useful as EP4 receptor antagonists for the treatment of EP4 receptor mediated diseases or conditions, such as acute and chronic pain, osteoarthritis, rheumatoid arthritis and cancer. Pharmaceutical compositions and methods of use are also included within the scope of the invention.

DETAILED DESCRIPTION OF THE INVENTION

Definitions

Abbreviations used herein have their conventional meaning within the chemical and biological arts.

"Alkyl" by itself or as part of another substituent, means, unless otherwise stated, a straight (i.e. unbranched) or branched chain, or cyclic hydrocarbon radical, or combination thereof, which may be fully saturated, mono- or polyunsaturated and can include di- and multivalent radicals. Having the number of carbon atoms designated (i.e. C1-C10) means one to ten carbons. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl".

"Fluoroalkyl" means alkyl as defined above wherein one or more hydrogen atoms have been replaced by fluoro atoms.

"Alkylene" by itself or as part of another substituent means a divalent radical derived from an alkyl, as exemplified by but not limited to, —CH2CH2CH2CH2-, —CH2CH=CHCH2-, —CH2C≡CCH2-, —CH2CH2CH (CH2CH2CH3)CH2-. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

"Alkynyl" means carbon chains which contain at least one carbon-carbon triple bond, and which may be linear or branched or combinations thereof Examples of alkynyl include ethynyl, propargyl, 3-methyl-1-pentynyl, 2-heptynyl and the like.

"Cycloalkyl" means mono- or bicyclic saturated carbocyclic rings, each of which having from 3 to 10 carbon atoms. A "fused analog" of cycloalkyl means a monocyclic ring fused to an aryl or heteroaryl group in which the point of attachment is on the non-aromatic portion. Examples of cycloalkyl and fused analogs thereof include cyclopropyl, cyclobutyl, cyclopentyl, cyclohexyl, cycloheptyl, tetrahydronaphthyl, decahydronaphthyl, indanyl, and the like.

"Alkoxy" means alkoxy groups of a straight or branched chain having the indicated number of carbon atoms. C1-6alkoxy, for example, includes methoxy, ethoxy, propoxy, isopropoxy, and the like.

"Heteroalkyl," by itself or in combination with another term, means, unless otherwise stated, a stable straight or branched chain, or cyclic hydrocarbon radical, or combinations thereof, consisting of at least one carbon atom and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom (s) O, N, P and S and Si may be placed at any interior position of the heteroalkyl group or at the position at which the alkyl group is attached to the remainder of the molecule. Examples include, but are not limited to, —CH2-CH2-O—CH3, —CH2-CH2-NH—CH3, —CH2-CH2-N(CH3)-CH3, —CH2-S—CH2-CH3, —CH2-CH2, —S(O)—CH3, —CH2-CH2-S(O) 2-CH3, —CH═CH—O—CH3, —Si (CH3)3, —CH2-CH═N—OCH3, —CH═CH—N(CH3)-CH3, —O—CH3, —O—CH2-CH3, and —CN. Up to two or three heteroatoms may be consecutive, such as, for example, —CH2-NH—OCH3 and —CH2-O—Si(CH3)3. Similarly, the term "heteroalkylene" by itself or as part of another substituent means a divalent radical derived from heteroalkyl, as exemplified, but not limited by, —CH2-CH2-S—CH2-CH2- and —CH2-S—CH2-CH2-NH—CH2-. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC (O)—. As described above, heteroalkyl groups, as used herein, include those groups that are attached to the remainder of the molecule through a heteroatom, such as —C(O)R', —C(O)NR', —NR'R", —OR', —SR', and/or —SO2R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cycloalkoxy" means cycloalkyl as defined above bonded to an oxygen atom, such as cyclopropyloxy.

"Fluoroalkoxy" means alkoxy as defined above wherein one or more hydrogen atoms have been replaced by fluoro atoms.

"Aryl" means mono- or bicyclic aromatic rings containing only carbon atoms. A "fused analog" of aryl means an aryl group fused to a monocyclic cycloalkyl or monocyclic heterocyclyl group in which the point of attachment is on the aromatic portion. Examples of aryl and fused analogs thereof include phenyl, naphthyl, indanyl, indenyl, tetrahydronaphthyl, 2,3-dihydrobenzofuranyl, dihydrobenzopyranyl, 1,4-benzodioxanyl, and the like.

"Heteroaryl" means a mono- or bicyclic aromatic ring containing at least one heteroatom selected from N, O and S, with each ring containing 5 to 6 atoms. A "fused analog" of heteroaryl means a heteroaryl group fused to a monocyclic cycloalkyl or monocyclic heterocyclyl group in which the point of attachment is on the aromatic portion. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo (2,3-b)pyridyl, quinolyl, indolyl, isoquinolyl, and the like.

The said aryl groups and said heteroaryl groups referred to in the definitions of Ar1 and Ar2 are unsubstituted or are substituted by at least one substituent selected from the group consisting of substituents a; the said substituents a are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms, cyano groups, alkynyl groups having from 2 to 6 carbon atoms, alkanoyl groups having from 1 to 5 carbon atoms, cycloalkyl groups having from 3 to 7 ring atoms, heteroaryl groups, aryl groups, aralkoxy groups having from 7 to 10 carbon atoms, arylcarbonyl groups, two adjacent-x groups are optionally joined together to form an alkylene or an alkenylene chain having 3 or 4 carbon atoms, aminocarbonyl groups, alkenyl groups having from 2 to 5 carbon atoms, alkylthio groups having from 1 to 4 carbon atoms, aminosulfinyl groups, aminosulfonyl groups, hydroxy groups, hydroxyalkyl groups having from 1 to 4 carbon atoms, nitro groups, amino groups, carboxy groups, alkoxycarbonyl groups having from 2 to 5 carbon atoms, alkoxyalkyl groups having from 1 to 4 carbon atoms, alkylsulfonyl groups having from 1 to 4 carbon atoms, alkanoylamino groups having from 1 to 4 carbon atoms, alkanoyl(alkyl) amino groups having from 1 to 6 carbon atoms, alkanoylaminoalkyl groups having from 1 to 6 carbon atoms in both the alkanoyl and alkyl part, alkanoyl(alkyl)aminoalkyl groups having from 1 to 6 carbon atoms in both the alkanoyl and each alkyl part, alkylsulfonylamino groups having from 1 to 4 carbon atoms, mono- or di-alkylaminocarbonyl groups having from 1 to 6 carbon atoms, mono- or di-alkylaminosulfinyl groups having from 1 to 6 carbon atoms, mono- or di alkylaminosulfonyl groups having from 1 to 6 carbon atoms, aminoalkyl groups having from 1 to 4 carbon atoms, mono- or di-alkylamino groups having from 1 to 6 carbon atoms, mono- or di-alkylaminoalkyl groups having from 1 to 6 carbon atoms in each alkyl part, aralkyl groups having from 7 to 10 carbon atoms, heteroarylalkyl groups having from 1 to 4 carbon atoms in the alkyl part, heteroarylalkoxy groups having from 1 to 4 carbon atoms in the alkoxy part and alkylsulfonylamino groups having from I to 4 carbon atoms.

"Heterocyclyl" means mono- or bicyclic saturated rings containing at least one heteroatom selected from N, S and O, each of said ring having from 3 to 10 atoms in which the point of attachment may be carbon or nitrogen. A "fused analog" of heterocyclyl means a monocyclic heterocycle fused to an aryl or heteroaryl group in which the point of attachment is on the non-aromatic portion. Examples of "heterocyclyl" and fused analogs thereof include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

"Halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C1-C4)alkyl" is mean to include, but not be limited to, trifluoromethyl, 2,2,2-trifluoroethyl, 4-chlorobutyl, 3-bromopropyl, and the like.

The term "concomitantly administering" means administering one or more therapeutic agents substantially concurrently. The term "concomitantly administering" encompasses not only administering two agents in a single pharmaceutical dosage form but also administration of each active agent in its own separate pharmaceutical dosage formulation. Where separate dosage formulations are used, the agents can be administered at essentially the same time, i.e., concurrently.

The term "sequentially administering" means administering agents at separately staggered times. Thus, for example, agents can be sequentially administered such that the beneficial pharmaceutical effect of aspirin and a compound of the present invention are realized by the patient at substantially the same time. Thus, for example, if a compound of the present invention and aspirin are both administered on a once a day basis, the interval of separation between sequential administration of the two agents can be up to twelve hours apart.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrugs may also have improved solubility in pharmaceutical compositions over the parent drug. An example, without limitation, of a prodrug would be a compound of Formula I, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug, again without intending to limit the scope of the term, might be one in which a short peptide is bonded to an acid group which is converted to the active moiety inside the cell.

The present invention provides in part compounds of Formula I, which are useful as EP4 selective antagonists:

Formula I or a pharmaceutically acceptable salt thereof, wherein:
R1, R2 are independently selected from the group consisting of hydrogen, C1-6alkyl, C1-6cyclolkyl, C1-6fluorocycloalkyl, C1-6fluoroalkyl; or R1, R2, together with the carbon atom to which they are both attached, complete a three- to six-membered carbocyclic ring which is optionally substituted with Rc; or R1 and R2 together with the carbon atom to which they are both attached complete a three- to six-membered ring which contains one or two heteroatom(s) such as S, O or NRb, wherein Rb is selected from the group consisting of hydrogen, C1-6alkyl, C1-6cyclolkyl, C1-6fluorocycloalkyl, C1-6fluoroalkyl, aryl, heteroaryl, C(O)C1-6alkyl, C(O)aryl, S(O)2alkyl, S(O)2aryl;
Y is O or S;
X is a bond, =CH—, CH2, O, or S;
Ar1 and Ar2 are independently selected from the group consisting of C3-6cycloalkyl, aryl, heteroaryl and heterocyclyl, or a fused analog of C3-6cycloalkyl, aryl, heteroaryl and heterocyclyl, wherein Ar1 and Ar2 are optionally substituted with one to three Rc groups;
Rc is independently selected from halo or R1,
Ra represents —CO2H, —CO2M, —C(O)NHS(O)2Raa, or

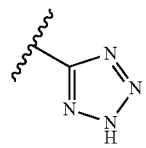

Raa is selected from C1-6alkyl, C1-6haloalkyl, C1-6cycloalkyl, C1-6cyclohaloalkyl, aryl and heteroaryl;
M is an ester prodrug group; and

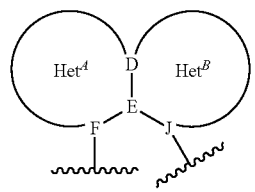

is a 6,6- 5,5- 5,6- or 6,5-bicyclic template.
In one embodiment,

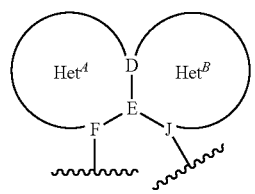

is selected from the following heterocyclic moieties:

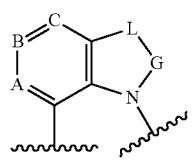

wherein each of A, B and C is independently selected from N, CH and C(Rc);
G is selected from —C(O), —C(S)—; or G is —S(O)2-;
L is selected from —CH2-, S, O and NRc.
In another embodiment,

7

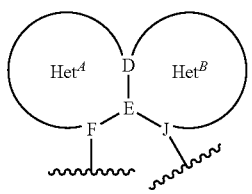

is selected from the following heterocyclic moieties:

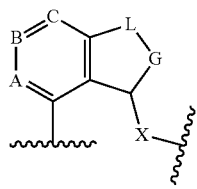

wherein each of A, B and C is independently selected from N, CH and C(Rc);

X, L and G are independently selected from a bond, —CH2-, O, S, or N(Rd);

Rd is H, aryl or alkyl.

In another embodiment,

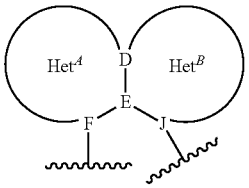

is selected from the following heterocyclic moieties:

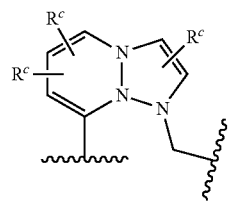

where Rc is as previously defined.

In another embodiment,

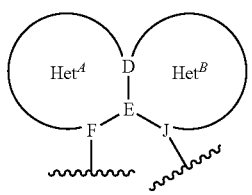

is selected from the following heterocyclic moieties:

8

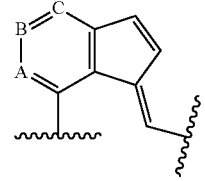

wherein each of A, B and C is independently selected from N, CH and C(Rc).

In another embodiment,

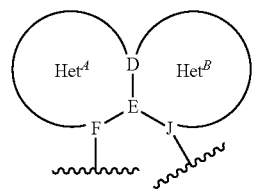

is selected from the following heterocyclic moiety:

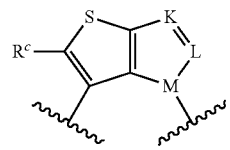

wherein —K-L-M- is selected from the group consisting of:
—C(R3)=C(R)—N—,
—C(R4)=N—C(R)—,
—C(R4)=N—N—,
—N=C(R4)-N—,
—C(R4)2-N=C—,
—N(R4)-C(R)=C—,
—N(R4)-N=C—,
—C(R3)=N—N—
—N=C(R3)-N—
—O—N=C— and
—S—N=C— wherein R3 is selected from the group consisting of hydrogen, halo, C1-6alkyl, C1-6fluoroalkyl, C1-6alkoxy, C1-6fluoroalkoxy and acetyl;

each R4 is independently selected from the group consisting of hydrogen, C1-6alkyl, C1-6fluoroalkyl, C1-6alkoxy, C1-4fluoroalkoxy and acetyl;

In another embodiment,

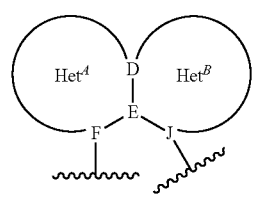

is selected from the following 6,5-hetero-bicyclic moieties:

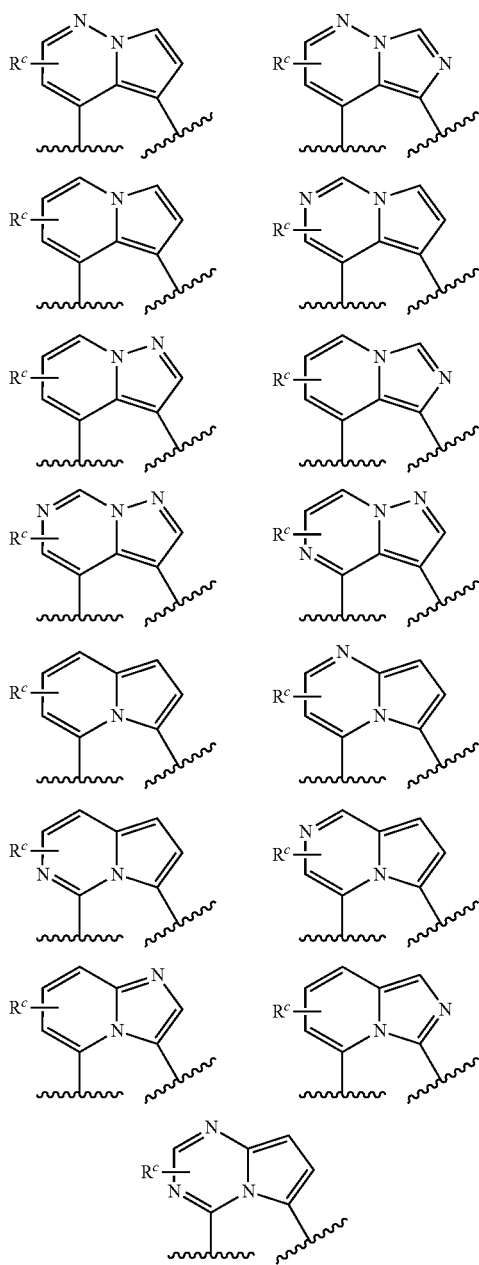

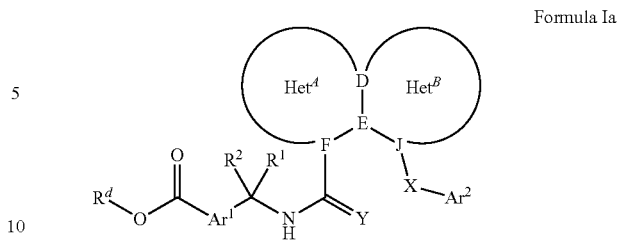

Formula Ia where Rd represents an alkyl group having 1 to 10 carbon atoms or an arakly group having from 7 to 12 carbon atoms, aryl, or heteroaryl.

Another preferred prodrug of Formula I is an ester derivative which contains one or more nitric oxide releasing groups (Formula Ib).

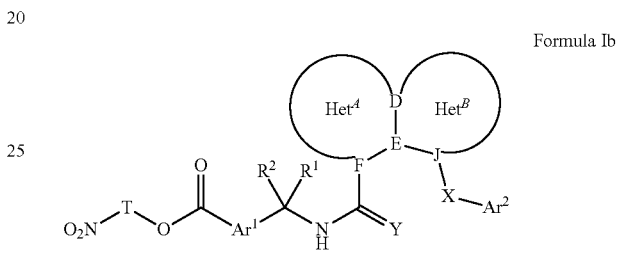

Formula Ib

Wherein
T is any suitable linker.
One embodiment of compounds of nitric oxide-releasing prodrugs of EP4 antagonists are those of Formula Ic.

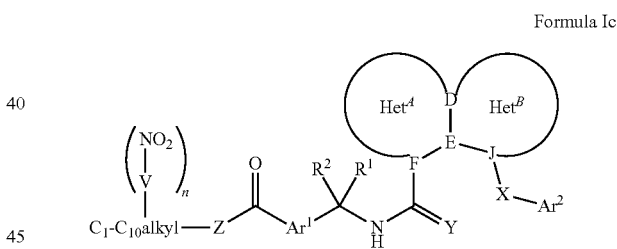

Formula Ic or a pharmaceutically acceptable salt thereof, wherein
Z is O, S or NRe, Re is hydrogen, alkyl or aryl;
V is independently selected from the group consisting of O and S. Each V is independently attached to any one carbon atom of the C1-C10alkyl;
n is 1, 2, 3 or 4.

Another embodiment of compounds of nitric oxide-releasing prodrugs of EP4 antagonists are those of Formula Id.

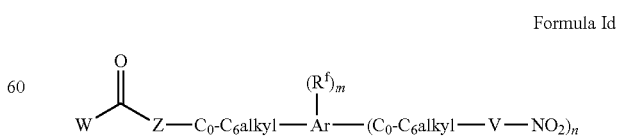

Formula Id wherein
Z is O, S or NRe; Re is hydrogen, alkyl or aryl;
V is O or S; each V is independently attached to one carbon atom of the C1-C10alkyl;

In one embodiment, the present invention relates to compounds of Formula I wherein R1 is methyl and R2 is hydrogen; or wherein R1 is methyl and R2 is methyl; or wherein R1 and R2 together with the carbon atom to which they both are attached form an three- to six-membered carbocyclic ring.

In another embodiment, the present invention relates to compounds of Formula I wherein Ar1 is phenyl, optionally substituted with one to three Re groups; or compounds of Formula I wherein Ar2 is phenyl, optionally substituted with one to three Rc groups.

The present invention also encompasses a prodrug of Formula I. The prodrug can be an ester or amide or other suitable group. Preferred prodrugs include an ester derivative of Formula Ia.

Rf is selected from the group consisting of hydrogen, halo, alkoxy, alkylthio, CN, CF3, alkyl, alkylsulfonyl, S(O)2NH2, and S(O)2NH-alkyl;

W is

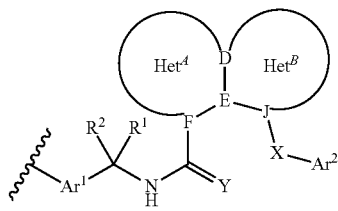

Preferably, compounds of nitric oxide releasing prodrugs of EP4 antagonists are those of Formula Ie, I(f) or I(g):

Formula Ie

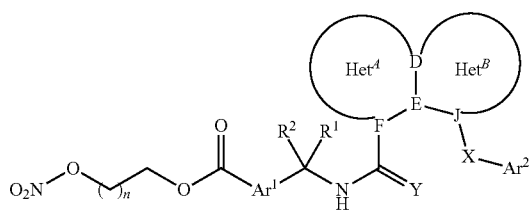

wherein n is an integer from 1 to 10.

Formula If

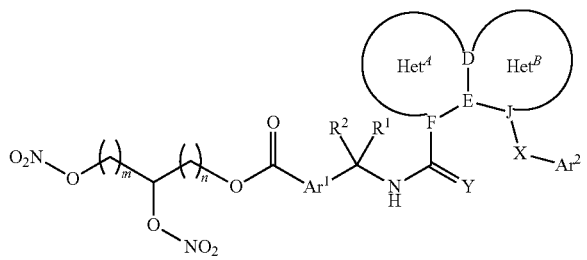

wherein n and m are an integer from 1 to 10;

Formula Ig

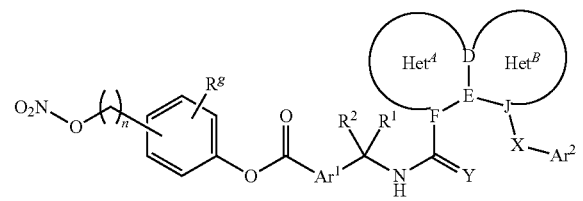

wherein n is integer of 1 to 6;
Rg is H, halogen, alkyl, haloalkyl.

It will be appreciated that certain compounds of Formula I (or salts, prodrugs, or conjugates) may exist in, and be isolated in, isomeric forms, including tautomeric forms, cis- or trans-isomers, as well as optically active, racemic, or diastereomeric forms. It is to be understood that the present invention encompasses a compound of Formula I in any of the tautomeric forms or as a mixture thereof; or as a mixture of diastereomers, as well as in the form of an individual diastereomers, and that the present invention encompasses a compound of Formula I as a mixture of enantiomers, as well as in the form of an individual enantiomer, any of which mixtures or form possesses antagonistic properties against EP4 receptor, it being well known in the art how to prepare or isolate particular forms and how to determine antagonistic properties against EP4 receptor by standard tests including those described herein below.

In addition, a compound of Formula I (or salt, prodrug or conjugate thereof) may exhibit polymorphism or may form a solvate with water or an organic solvent. The present invention also encompasses any such polymorphic form, any solvate or any mixture thereof.

As mentioned above, the invention includes a pharmaceutically acceptable salt of a compound of Formula I. A basic compound of this invention possesses one or more functional groups sufficiently basic to react with any of a number of inorganic and organic acids affording a physiologically acceptable counterion to form a pharmaceutically acceptable salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like.

The invention also encompasses other acceptable forms of prodrugs of Formula I formed in a conventional manner with a functional group of the compound such as with an amino, hydroxy, or carboxy group.

The invention also relates to a method for antagonizing EP4 receptor by administering an effective amount of a compound of Formula I.

The invention also encompasses a method of treating a human or animal subject suffering from a condition which is mediated by the action of PGE2 at EP4 receptors, which method comprises administering to said subject an effective amount of a compound of Formula I.

The invention also encompasses use of a compound of Formula I for the manufacture of a medicament for the treatment of a disease or condition that is mediated by the action of PGE2 at EP4 receptors.

Optical Isomers—Diastereomers—Geometric Isomers—Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I to Formula Ig.

Some of the compounds described herein contain olefinic double bonds, and unless specified otherwise, are meant to include both E and Z geometric isomers.

Compounds described herein may exist with different points of attachment of hydrogen, referred to as tautomers. For example, a ketone and its enol form are known as keto-enol tautomers. The individual tautomers as well as mixtures thereof are encompassed with compounds of Formula I to Formula Ig.

Compounds of Formula I may be separated into diastereoisomeric pairs of enantiomers by, for example, fractional crystallization from a suitable solvent, such as MeOH or EtOAc or a mixture thereof Enantiomers thus obtained may be separated into individual stereoisomers by conventional means, for example by use of an optically active amine as a resolving agent, or on a chiral HPLC column.

Alternatively, any enantiomer of a compound of Formula I may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methyl-glucamine, morpholine, piperazine, piperidine, polyamine resins, procaine, purines, theobromine, triethylamine, trimethylamine, tripropylamine, tromethamine, and the like.

When a compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Utilities

Compounds of the present invention are antagonists of the EP4 receptor and are therefore expected to be useful in treating EP4 receptor mediated diseases. In one embodiment, the prodrugs of EP4 antagonists described in this invention including those of Formula I have an antagonistic action towards prostaglandin upon in vivo biotransformation and are thus useful in therapeutics, particularly for the treatment of diseases or conditions such as, pain, neuropathic pain, visceral pain, inflammatory pain, nociceptive pain, chronic pain, acute pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, fibromyalgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures, bone fracture, immune and autoimmune diseases; cellular neoplastic transformations or metastic tumor growth; diabetic retinopathy, tumor angiogenesis; prostanoid-induced smooth muscle contraction associated with dysmenorrhea, premature labor, allergic rhinitis, atopic dermatitis, asthma or eosinophil related disorders, hyperimmunoglobulinaemia, Castleman's disease, myeloma; Alzheimer's disease, sleep disorders, endocrine disturbance; glaucoma; bone loss; osteoporosis, promotion of bone formation; Paget's disease: cytoprotection in peptic ulcers, gastritis, regional enteritis, ulcerative colitis, diverticulitis or other gastrointestinal lesions; GI bleeding and patients undergoing chemotherapy; coagulation disorders selected from hypoprothrombinemia, haemophilia, other bleeding problems; kidney disease; thrombosis; occlusive vascular disease; presurgery; and anti-coagulation; sympathetically maintained pain; pain resulting I from amputation, skin conditions (e.g. eczema, psoriasis); ophthalmic diseases such as glaucoma, retinitis, retinopathies, uveitis and of acute injury to the eye tissue (e.g. conjunctivitis); lung disorders (e.g. bronchitis, emphysema, allergic rhinitis, respiratory distress syndrome, pigeon fancier's disease, farmer's lung, COPD); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastrointestinal reflex disease); organ transplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, tendonitis, bursitis, and Sjogren's; abnormal platelet function (e.g. occlusive vascular diseases); diuretic action; impotence or erectile dysfunction; bone disease characterised by abnormal bone metabolism or resorption such as osteoporosis; hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis (especially urolithiasis), solid carcinoma, gout and ankylosing spondylitis, tendinitis and bursitis; bone resorption, the hemodynamic side effects of NSAIDs and COX-2 inhibitors, cardiovascular diseases, hypertension or myocardiac ischemia; functional or organic venous insufficiency; varicose therapy; haemorrhoids; and shock states associated with a marked drop in arterial pressure (e.g. septic shock); neurodegenerative diseases and neurodegeneration such as dementia, particularly degenerative dementia (including senile dementia, Alzheimer's disease, Pick's disease, Huntingdon's chores, Parkinson's disease and Creutzfeldt-Jakob disease, ALS, motor neuron disease); vascular dementia (including multi-infarct dementia); as well as dementia associated with intracranial space occupying lesions; trauma; infections and related conditions (including HIV infection); metabolism; toxins; anoxia and vitamin deficiency; and mild cognitive impairment associated with aging, particularly Age Associated Memory Impairment; neuroprotection, neurodegeneration following stroke, cardiac arrest, pulmonary bypass, traumatic brain injury, spinal cord injury; tinnitus, complications of Type 1 diabetes (e.g. diabetic microangiopathy, I diabetic nephropathy, macular degeneration, glaucoma), nephrotic syndrome, aplastic anaemia, uveitis, Kawasaki disease and sarcoidosi; kidney dysfuncion (e.g. nephritis particularly mesangial proliferative glomerulonephritis, nephritic syndrome), liver dysfunction (hepatitis, cirrhosis), gastrointestinal dysfunction (diarrhea), alcoholic cirrhosis, amyloidosis, atherosclerosis, cardiac disease, sclerosis, organ transplantation reactions, glucocorticoid induced osteoporosis, tooth loss, bone fractures, multiple myeloma, various edema, hypertension, premenstrual tension, I urinary calculus, oliguria, hyperphosphaturia, prutitus urticaria, contact-type dermatitis, rhus dermatitis, pollakiuria, learning disability, gingiritis, predontitis, lung injury, liver injury, and constipation, or the like in mammalian subjects, including humans.

The present invention also encompasses a method of treating an inflammatory disease susceptible to treatment with a non-steroidal anti-inflammatory agent comprising administering to a patient in need of such treatment a non-toxic therapeutically effective amount of a compound of Formula I. Within this embodiment is encompassed the above method wherein the patient is also at risk of a thrombotic cardiovascular event and/or GI ulceration/bleeding.

Another embodiment of the present invention relates to a method of treating prostaglandin E2 mediated diseases advantageously treated by an active agent that selectively antagonizes EP4 in preference to COX-1/COX-2 inhibition, comprising administering to a patient in need of such treatment of a non-toxic therapeutically effective amount of a compound of Formula I. This embodiment of the invention includes therapies wherein the patient is also at risk of a thrombotic cardiovascular event.

Another embodiment of the present invention relates to a method for treating a chronic prostaglandin E2 mediated disease or condition while reducing the risk of a thrombotic cardiovascular and GI bleeding event in a human patient in need of such treatment comprising concomitantly, or sequentially administering to said patient a compound of Formula I in an amount effective to treat the prostaglandin E2 mediated disease or condition, and aspirin in an amount effective to reduce the risk of the thrombotic cardiovascular event. Within this embodiment is encompassed the above method wherein the compound of Formula I is administered orally on a once or twice daily basis. This embodiment includes treating osteoarthritis, rheumatoid arthritis, chronic pain and cancer. In this embodiment aspirin is administered at a dose of about 30 mg to about 1000 mg; about 80 mg to about 650 mg; or about 81 mg to about 325 mg. In one aspect of this embodiment, aspirin is orally administered once daily.

The present invention also encompasses a pharmaceutical composition comprising a compound of Formula I and aspirin in combination with a pharmaceutically acceptable carrier.

The term "treating a chronic Prostaglandin E2 mediated disease or condition" means treating or preventing any chronic disease or condition that is advantageously treated or prevented by administering a selective EP4 antagonist of the present invention. The term includes the relief of pain, fever and inflammation of a variety of conditions including rheumatic fever, symptoms associated with influenza or other viral infections, common cold, low back pain, neck pain, dysmenorrhea, headache, migraine, toothache, sprains and strains, myositis, neuralgia, synovitis, arthritis, including rheumatoid arthritis, degenerative joint diseases (osteoarthritis), gout, ankylosing spondylitis, bursitis, burns, injuries, and pain and inflammation following surgical procedures. In addition, compounds of the invention may inhibit cellular neoplastic transformations and metastatic tumor growth and hence can be used in the treatment and/or prevention of cancer. In addition, compounds of the invention may inhibit the onset or progression of Alzheimer's disease or cognitive impairment. The term also includes the treatment and/or prevention of prostaglandin E2-mediated proliferative disorders such as may occur in diabetic retinopathy and tumor angiogenesis. The term "treating" encompasses not only treating a patient to relieve the patient of the signs and symptoms of the disease or condition but also prophylactically treating an asymptomatic patient to prevent the onset or progression of the disease or condition.

A "thrombotic cardiovascular event" is defined as any sudden event of a type known to be caused by platelet aggregation, thrombosis, and subsequent ischemic clinical events, including thrombotic or thromboembolic stroke, myocardial ischemia, myocardial infarction, angina pectoris, transient ischemic attack (TIA; amaurosis fugax), reversible ischemic neurologic deficits, and any similar thrombotic event in any vascular bed (splanchnic, renal, aortic, peripheral, etc.).

The term "patient in need of such treatment and at risk of a thrombotic cardiovascular event" means a patient in need of both treatment for a cyclooxygenase-2 mediated disease and also at risk of a thrombotic cardiovascular event. One skilled in the art can diagnose a patient that is in need of treatment for a cyclooxygenase-2 mediated disease or condition and also at risk of suffering a thrombotic cardiovascular event. For example, such a patient may be over the age of 50 with osteoarthritis and with a previous myocardial infarction. Other risk factors for a thrombotic cardiovascular event include hypertension, hypercholesterolemia, diabetes mellitus, chronic renal impairment, smoking, and any prior personal or family history of such an event. Administration of the drug combination to the patient includes both self-administration and administration to the patient by another person.

The compounds of the present invention are also useful for attenuating the hemodynamic side effects of NSAIDs and COX-2 inhibitors.

The compounds of the present invention are also useful in the treatment of cardiovascular diseases such as hypertension or myocardiac ischemia; functional or organic venous insufficiency; varicose therapy; haemorrhoids; and shock states associated with a marked drop in arterial pressure (e.g. septic shock).

The compounds of the present invention are also useful in the treatment of neurodegenerative diseases and neurodegeneration such as dementia, particularly degenerative dementia (including senile dementia, Alzheimer's disease, Pick's disease, Huntingdon's chores, Parkinson's disease and Creutzfeldt-Jakob disease, ALS, motor neuron disease); vascular dementia (including multi-infarct dementia); as well as dementia associated with intracranial space occupying lesions; trauma; infections and related conditions (including HIV infection); metabolism; toxins; anoxia and vitamin deficiency; and mild cognitive impairment associated with ageing, particularly Age Associated Memory Impairment.

The compounds of Formula I are also useful in the treatment of neuroprotection and in the treatment of neurodegeneration following stroke, cardiac arrest, pulmonary bypass, traumatic brain injury, spinal cord injury or the like.

The compounds of the present invention are also useful in the treatment of tinnitus.

The compounds of the present invention are also useful in preventing or reducing dependence on, or preventing or reducing tolerance or reverse tolerance to, a dependence-inducing agent. Examples of dependence inducing agents include opioids (e.g. morphine), CNS depressants (e.g. ethanol), psychostimulants (e.g. cocaine) and nicotine.

The compounds of the present invention are also useful in the treatment of complications of Type 1 diabetes (e.g. diabetic microangiopathy, diabetic retinopathy, diabetic nephropathy, macular degeneration, glaucoma), nephrotic syndrome, aplastic anaemia, uveitis, Kawasaki disease and sarcoidosis.

The compounds of the present invention are also useful in the treatment of kidney dysfunction (nephritis, particularly mesangial proliferative glomerulonephritis, nephritic syndrome), liver dysfunction (hepatitis, cirrhosis), gastrointestinal dysfunction (diarrhoea) and colon cancer.

The compounds of the present invention are also useful for treating or preventing a neoplasia in a subject in need of such treatment or prevention. The term "treatment" includes partial or total inhibition of the neoplasia growth, spreading or metastasis, as well as partial or total destruction of the neoplastic cells. The term "prevention" includes either preventing the onset of clinically evident neoplasia altogether or preventing the onset of a preclinically evident stage of neoplasia in individuals at risk. Also intended to be encompassed by this definition is the prevention of initiation for malignant cells or to arrest or reverse the progression of premalignant cells to malignant cells. This includes prophylactic treatment of those at risk of developing the neoplasia. The term "subject" for purposes of treatment includes any human or mammal subject who has any one of the known neoplasias, and preferably is a human subject. For methods of prevention, the subject is any human or animal subject, and preferably is a human subject who is at risk for obtaining a neoplasia. The subject may be at risk due to exposure to carcinogenic agents, being genetically predisposed to have the neoplasia, and the like.

The term "neoplasia" includes both benign and cancerous tumors, growths and polyps. Thus, the compounds of the invention are useful for treating or preventing benign tumors, growths and polyps including squamous cell papilloma, basal cell tumor, transitional cell papilloma, adenoma, gastrinoma, cholangiocellular adenoma, hepatocellular adenoma, renal tubular adenoma, oncocytoma, glomus tumor, melanocytic nevus, fibroma, myxoma, lipoma, leiomyoma, rhabdomyoma, benign teratoma, hemangioma, osteoma, chondroma and meningioma. The compounds of the invention are also useful for treating or preventing cancerous tumors, growths and polyps including squamous cell carcinoma, basal cell carcinoma, transitional cell carcinoma, adenocarcinoma, malignant gastrinoma, cholangiocelleular carcinoma, hepatocellular carcinoma, renal cell carcinoma, malignant melanoma, fibrosarcoma, myxosarcoma, liposarcoma, leimyosarcoma, rhabdomyosarcoma, malignant teratoma, hemangiosarcoma, Kaposi sarcoma, lymphangiosarcoma, ostreosarcoma, chondrosarcoma, malignant meningioma, non-Hodgkin lymphoma, Hodgkin lymphoma and leukemia. For purposes of this specification, "neoplasia" includes brain cancer, bone cancer, epithelial cell-derived neoplasia (epithelial carcinoma), basal cell carcinoma, adenocarcinoma, gastrointestinal cancer such as lip cancer, mouth cancer, esophogeal cancer, small bowel cancer and stomach cancer, colon cancer, rectal cancer, liver cancer, bladder cancer, pancreas cancer, ovary cancer, cervical cancer, lung cancer, breast cancer and skin cancer, such as squamus cell and basal cell cancers, prostate cancer, renal cell carcinoma, and other known cancers that affect epithelial, mesenchymal or blood cells throughout the body. The compounds of the invention are useful for treating or preventing any of the aforementioned cancers. The compounds of the invention are useful for treating or preventing benign and cancerous tumors, growths and polyps of the following cell types: squamous epithelium, basal cells, transitional epithelium, glandular epithelium, G cells, bile ducts epithelium, hepatocytes, tubules epithelium, melanocytes, fibrous connective tissue, cardiac skeleton, adipose tissue, smooth muscle, skeletal muscle, germ cells, blood vessels, lymphatic vessels, bone, cartilage, meninges, lymphoid cells and hematopoietic cells. The compounds can be used to treat subjects having adenomatous polyps, including those with familial adenomatous polyposis (FAP). Additionally, the compounds can be used to prevent polyps from forming in patients at risk of FAP. Preferably, the compounds of the invention are useful for treating or preventing the following cancers: colorectal, esophagus stomach, breast, head and neck, skin, lung, liver, gall bladder, pancreas, bladder, endometrium cervix, prostate, thyroid and brain.

Compounds of Formula I can also be used in combination with one or more chemotherapeutic agents such as:

i. an aromatase inhibitor, ii. an antiestrogen, an anti-androgen (especially in the case of prostate cancer) or a gonadorelin agonist, iii. a topoisomerase I inhibitor or a topoisomerase II inhibitor, iv. a microtubule active agent, an alkylating agent, an antineoplastic antimetabolite or a platin compound, v. a compound targeting/decreasing a protein or lipid kinase activity or a protein or lipid phosphatase activity, a further anti-angiogenic compound or a compound which induces cell differentiation processes, vi. a bradykinin I receptor or an angiotensin II antagonist, vii. a cyclooxygenase inhibitor, a bisphosphonate, a rapamycin derivative such as everolimus, a heparanase inhibitor (prevents heparan sulphate degradation), e.g. P1 88, a biological response modifier, preferably a lymphokine or interferons, e.g. interferon if, an ubiquitination inhibitor, or an inhibitor which blocks anti-apoptotic pathways, viii. an inhibitor of Ras oncogenic isoforms, e.g. H-Ras, K-Ras or N-Ras, or a farnesyl transferase inhibitor, e.g. L-744, 832 or DK8G557, ix. a telomerase inhibitor, e.g. telomestatin, x. a protease inhibitor, a matrix metalloproteinase inhibitor, a methionine aminopeptidase inhibitor, e.g. bengamide or a derivative thereof, or a proteosome inhibitor, e.g. PS 341, xi. histone deacetylase inhibitors, e.g. Vorinostat, MG0103 or MS275.

xii. PTP 1B inhibitors.

It is to be understood that reference to treatment includes both treatment of established symptoms and prophylactic treatment, unless explicitly stated otherwise.

The terms "nitric oxide releasing-EP4 antagonist" or "NO-EP4 antagonist," mean a modified version of a selective EP4 antagonist prodrug as defined herein linked to a NO releasing moiety by means of a linking group such as an ester linkage.

The term "amounts that are effective to treat" is intended to mean that amount of a drug or pharmaceutical agent that will elicit the biological or medical response of a tissue, a system, animal or human that is being sought by a researcher, veterinarian, medical doctor or other clinician. The term also encompasses the amount of a pharmaceutical drug that will prevent or reduce the risk of occurrence of the biological or medical event that is sought to be prevented in a tissue, a system, animal or human by a researcher, veterinarian, medical doctor or other clinician. The NO-EP4 antagonist may be administered at a dosage level up to conventional dosage levels for NSAIDs. Suitable dosage levels will depend upon the antiinflammatory effect of the chosen EP4 antagonist, but typically suitable levels will be about 0.001 to 50 mg/kg per day, preferably 0.005 to 30 mg/kg per day, and especially 0.05 to 10 mg/kg per day. The compound may be administered on a regimen of once, twice or three times per day.

Formulations

The present invention also provides a pharmaceutical composition for use in the above-described therapeutic methods. Pharmaceutical compositions of the present invention comprise a compound of Formula I as an active ingredient or a pharmaceutically acceptable salt, thereof, in an amount sufficient to antagonize EP4 receptor, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

It will be understood that in the discussion of methods of treatment herein references to the compounds of Formula I are meant to also include the pharmaceutically acceptable salts.

Compounds of Formula I will also inhibit prostaglandin E2-induced smooth muscle contraction by preventing the synthesis of contractile prostanoids and hence may be of use in the treatment of dysmenorrhea, premature labor and asthma. They will also be useful to inhibit bone loss (osteoporosis).

Similarly, compounds of Formula I, will be useful as a partial or complete substitute for conventional NSAID'S in preparations wherein they are presently co-administered with other agents or ingredients. Thus in further aspects, the invention encompasses pharmaceutical compositions for treating Prostaglandin E2 mediated diseases as defined above comprising a non-toxic therapeutically effective amount of the compound of Formula I as defined above and one or more ingredients such as another pain reliever including NSAIDs, COX-2 selective inhibitors, acetaminophen or phenacetin; a potentiator including caffeine; an H2-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antitussive including codeine, hydrocodone, caramiphen, carbetapentane, or dextramethorphan; a diuretic; a sedating or non-sedating antihistamine. In addition the invention encompasses a method of treating cyclooxygenase mediated diseases comprising: administration to a patient in need of such treatment a non-toxic therapeutically effect amount of the compound of Formula I, optionally co-administered with one or more of such ingredients as listed immediately above.

Pharmaceutical compositions containing an active ingredient (i.e. a compound of Formula I) may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874, the contents of which are herein incorporated by reference, to form osmotic therapeutic tablets for controlled release.

The following formulation examples are illustrative only and are not intended to limit the scope of the invention in any way. The phrase "active ingredient" refers herein to a compound according to formula I or a pharmaceutically acceptable salt, procompound, conjugate, or solvate thereof.

Formulation 1: Tablet containing the following components:

| Ingredient | Amount (mg/tablet) |
| --- | --- |
| Active ingredient | 250 |
| Dried starch | 200 |
| Magnesium stearate | 10 |
| Total | 460 mg |

Formulation 2: Capsules containing the following components:

| Ingredient | Amount (mg/tablet) |
| --- | --- |
| Active ingredient | 60 |
| Dried starch | 44 |
| Magnesium stearate | 1.5 |
| Microcrystalline cellulose | 44 |
| Total | 150 mg |

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxypropylmethy-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an I atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns).

This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as 1-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from log to 20 mg of the compound of the invention per actuation and the actuation volume may vary from 1 l to 100 l. A typical formulation may comprise a compound of formula (1), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 fig to 10 mg of the compound of formula (I). The overall daily dose will typically be in the range 1 lag to 10 mg which may be administered in a single dose or, more usually, as divided doses throughout the day.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day, preferably 2.5 mg to 1 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular disease and/or patient will depend upon a variety of factors including the age, body weight, general health, sex, diet, time of administration, route of administration, rate of excretion, drug combination and the severity of the particular disease undergoing therapy.

Combination Therapy

Compounds of Formula I may be used in combination with other drugs useful in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to: COX-2 inhibitors, such as celecoxib, rofecoxib, etoricoxib, valdecoxib or parecoxib; 5-lipoxygenase inhibitors; NSAIDs, such as diclofenac, indomethacin, nabumetone or ibuprofen; leukotriene receptor antagonists; DMARDs such as methotrexate; adenosine A1 receptor agonists; sodium channel blockers, such as lamotrigine; NMDA receptor modulators, such as glycine receptor antagonists; gabapentin and related compounds; tricyclic antidepressants such as amitriptyline; neurone stabilising antiepileptic drugs; monoaminergic uptake inhibitors such as venlafaxine; opioid analgesics; local anaesthetics; 5HT agonists, such as triptans, for example sumatriptan, naratriptan, zolmitriptan, eletriptan, frovatriptan, almotriptan or rizatriptan; EP1 receptor ligands; EP2 receptor ligands; EP3 receptor ligands; EP1 antagonists; EP2 antagonists and EP3 antagonists; and Calcitonin gene-related peptide receptor antagonists. When compounds of the invention are used in combination with other therapeutic agents, the compounds may be administered either sequentially or simultaneously by any convenient route.

The invention thus provides, in a further aspect, a combination comprising a compound of Formula I or a pharmaceutically acceptable derivative or salt thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

The weight ratio of a compound of Formula I to a second active ingredient may be varied and will depend upon the effective dose of each ingredient. Generally, an effective dose of each will be used. Thus, for example, when a compound of Formula I is combined with an NSAID the weight ratio of the compound of Formula I to the NSAID will generally range from about 1000:1 to about 1:1000, preferably about 200:1 to about 1:200. Combinations of a compound of Formula I and other active ingredients will generally also be within the aforementioned range, but in each case, an effective dose of each active ingredient is preferred.

Assays For Determining Biological Activity

The compounds of Formula I can be tested using the following assays to determine their prostanoid antagonist or agonist activity in vitro and in vivo and their selectivity. The prostaglandin receptor activities demonstrated are DP, EP1, EP2, EP3, EP4, FP, IP and TP.

EXAMPLE A

Stable Expression of Prostanoid Receptors in the Human Embryonic Kidney (HEK) 293(ebna) Cell Line Prostanoid receptor cDNAs corresponding to full length coding sequences are subcloned into the appropriate sites of mammalian expression vectors and transfected into HEK 293 (ebna) cells. HEK 293(ebna) cells expressing the individual cDNAs are grown under selection and individual colonies are isolated after 2-3 weeks of growth using the cloning ring method and subsequently expanded into clonal cell lines.

EXAMPLE B

Prostanoid Receptor Binding Assays

Transfected HEK 293(ebna) cells are maintained in culture, harvested and membranes are prepared by differential centrifugation, following lysis of the cells in the presence of protease inhibitors, for use in receptor binding assays. Prostanoid receptor binding assays (for DP1, DP2 (CRTH2), EP1, EP2, EP3-III, EP4, FP, IP, and TP) are performed in 10 mM MES/KOH (pH 6.0) (EPs, FP and TP) or 10 mM HEPES/KOH (pH 7.4) (DPs and IP), containing 1 mM EDTA, 2.5-30 mM divalent cation and the appropriate radioligand. Synthetic compounds are added in dimethylsulfoxide which is kept constant at 1% (v/v) in all incubations. The reaction is initiated by addition of membrane protein. Non-specific binding is determined in the presence of 10 µM of the corresponding non-radioactive prostanoid. Incubations are conducted for 60-90 min at room temperature or 30° C. and terminated by rapid filtration. Specific binding is calculated by subtracting non specific binding from total binding. The residual specific binding at each ligand concentration is calculated and expressed as a function of ligand concentration in order to construct sigmoidal concentration-response curves. The binding affinity of the compounds is determined by calculating the equilibrium inhibition constant (Ki) from the equation Ki=InPt/1[radioligand]/Kd where Kd is the equilibrium dissociation constant for the radioligand:receptor interaction and InPt is the inflection point of the dose-response curves.

EP4 receptor binding assays were performed at MSD Pharma Service in Taiwan under the following assay conditions:

| | |
|---|---|
| Source: | Human recombinant Chem-1-cells |
| Ligand: | 1 nM [$^3$H] Prostaglandin $E_2$ ($PGE_2$) |

-continued

| | |
|---|---|
| Vehicle: | 1% DMSO |
| Incubation Time/Temp: | 2 hours @ 25° C. |
| Incubation Buffer: | 10 mM MES, pH 6.0, 1 mM EDTA, 10 mM MgCl |
| Non-Specific Ligand: | 10 μM Prostaglandin $E_2$ ($PGE_2$) |
| KD: | 0.69 nM |
| Bmax: | 4.3 pmol/mg Protein* |
| Specific binding: | 90% |
| Quantitation Method: | Radioligand binding |
| Significance Criteria: | >50% minimum inhibition |

TABLE 1

Inhibition of PGE2 Binding of Representative Compounds

| Compound | Tested Concentration | % inhibition of PGE2 binding |
|---|---|---|
|  | 2 nM | 88% |
|  | 2 nM | 93% |
|  | 10 nM | 85% |

TABLE 1-continued

Inhibition of PGE2 Binding of Representative Compounds

| Compound | Tested Concentration | % inhibition of PGE2 binding |
|---|---|---|
| 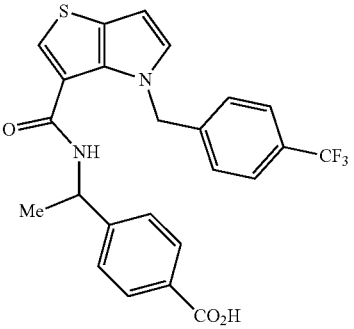 [SMILES: CC(NC(=O)c1csc2ccn(Cc3ccc(C(F)(F)F)cc3)c12)c1ccc(C(=O)O)cc1] | 10 nM | 87% |
| 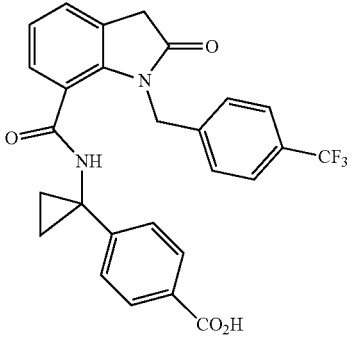 [SMILES: O=C(O)c1ccc(C2(NC(=O)c3cccc4c3N(Cc3ccc(C(F)(F)F)cc3)C(=O)C4)CC2)cc1] | 10 nM | 83% |

EXAMPLE C

Prostanoid Receptor Agonist and Antagonist Assay

Whole cell second messenger assays measuring stimulation of intracellular cAMP accumulation in HEK-293(ebna)-hEP4 cells are performed to determine whether receptor ligands are agonists or antagonists. Cells are harvested and resuspended in HBSS containing 25 mM HEPES, pH 7.4. Incubations contain 0.5 mM IBMX (phosphodiesterase inhibitor, available from Biomol). Samples are incubated at 37° C. for 10 min, the reaction is terminated and cAMP levels are then measured. Ligands are added in dimethylsulfoxide which is kept constant at 1% (v/v; agonists) or 2% (v/v; antagonists) in all incubations. For agonists, second messenger responses are expressed as a function of ligand concentration and both EC50 values and the maximum response as compared to a PGE2 standard are calculated. For antagonists, the ability of a ligand to inhibit an agonist response is determined by carrying out dose-response curves in the presence of PGE2 agonist at a concentration corresponding to its EC70. IC50 values are calculated as the concentration of ligand required to inhibit 50% of the PGE2-induced activity.

EXAMPLE D

Rat Paw Edema Assay

The method is the same as described in Chan et al (J. Pharmacol. Exp. Ther. 274: 1531-1537, 1995).

EXAMPLE E

Acute Inflammatory Hyperalgesia Induced by Carrageenan in Rats

The method is as described in Boyce et al (Neuropharmacology 33: 1609-1611, 1994) herein incorporated by reference.

EXAMPLE F

Adjuvant-Induced Arthritis in Rats

Female Lewis rats (body weight ~146-170 g) are weighed, ear marked, and assigned to groups (a negative control group in which arthritis was not induced, a vehicle control group, a positive control group administered indomethacin at a total daily dose of 1 mg/kg and four groups administered with a test compound at total daily doses of 0.10-3.0 mg/kg) such that the body weights were equivalent within each group. Six groups of 10 rats each are injected into a hind paw with 0.5 mg of *Mycobacterium* butyricum in 0.1 mL of light mineral oil (adjuvant), and a negative control group of 10 rats was not injected with adjuvant. Body weights, contralateral paw volumes (determined by mercury displacement plethysmography) and lateral radiographs (obtained under Ketamine and Xylazine anesthesia) are determined before (day −1) and 21 days following adjuvant injection, and primary paw volumes are determined before (day −1) and on days 4 and 21 following adjuvant injection. The rats are anesthetized with an intramuscular injection of 0.03-0.1 mL of a combination of Ketamine (87 mg/kg) and Xylazine (13 mg/kg) for radiographs and injection of adjuvant. The radiographs are made of both hind paws on day 0 and day 21 using the Faxitron (45 kVp, 30 seconds) and Kodak X-OMAT TL film, and are developed in an automatic processor. Radiographs are evaluated for changes in the soft and hard tissues by an investigator who was blinded to experimental treatment. The following radiographic changes are graded numerically according to severity: increased soft issue volume (0-4), narrowing or widening of joint spaces (0-5) subchondral erosion (0-3), periosteal reaction (0-4), osteolysis (0-4) subluxation (0-3), and degenerative joint changes (0-3). Specific criteria are used to establish the numerical grade of severity for each radiographic change. The maximum possible score per foot was 26. A test compound at total daily doses of 0.1, 0.3, 1, and 3 mg/kg/day, indomethacin at a total daily dose of 1 mg/kg/day, or vehicle (0.5% methocel in sterile water) are administered per os b.i.d. beginning post injection of adjuvant and continuing for 21 days. The compounds are prepared weekly, refrigerated in the dark until used, and vortex mixed immediately prior to administration.

Synthesis of Compounds

Scheme 1

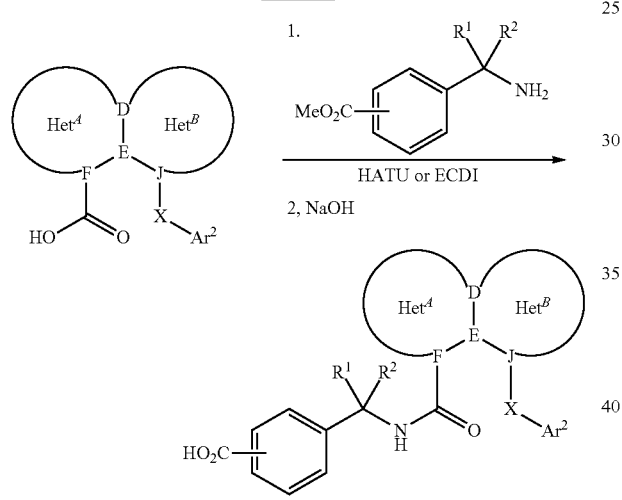

Scheme 2:

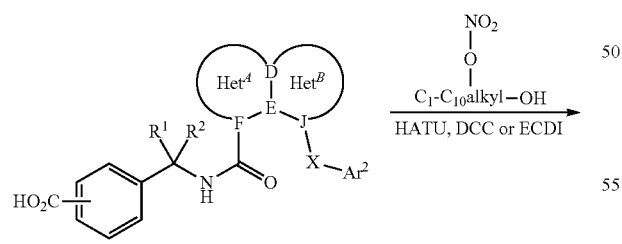

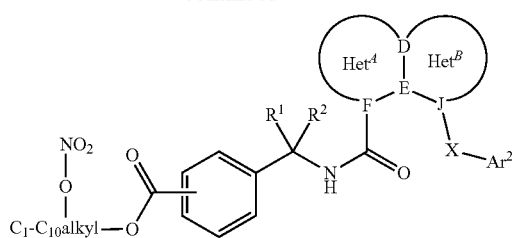

Scheme 3:

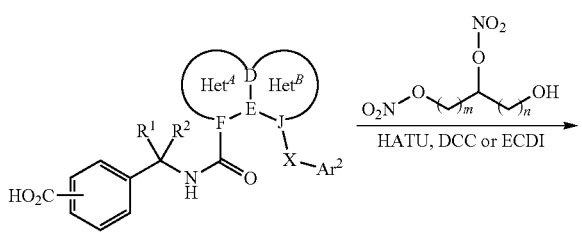

$n, m = 1$ to $10$

Scheme 4:
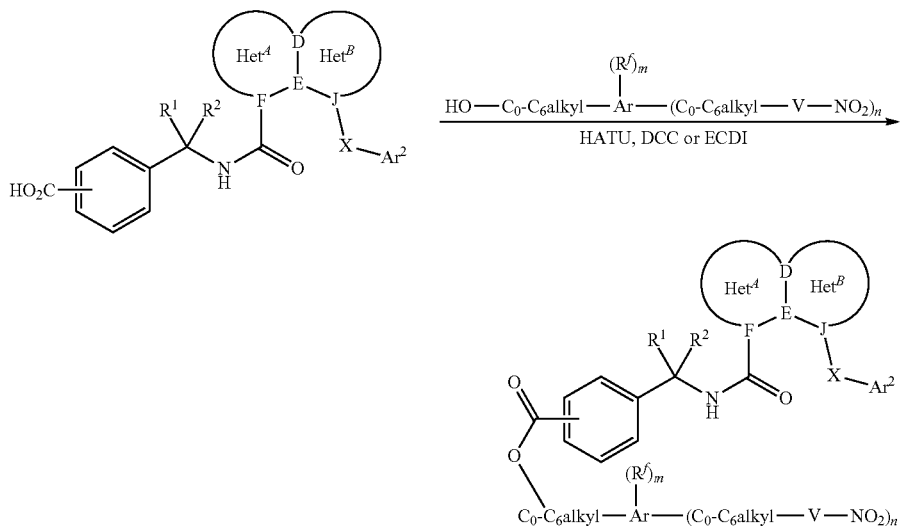
n, m = 1 to 4
Scheme 5:
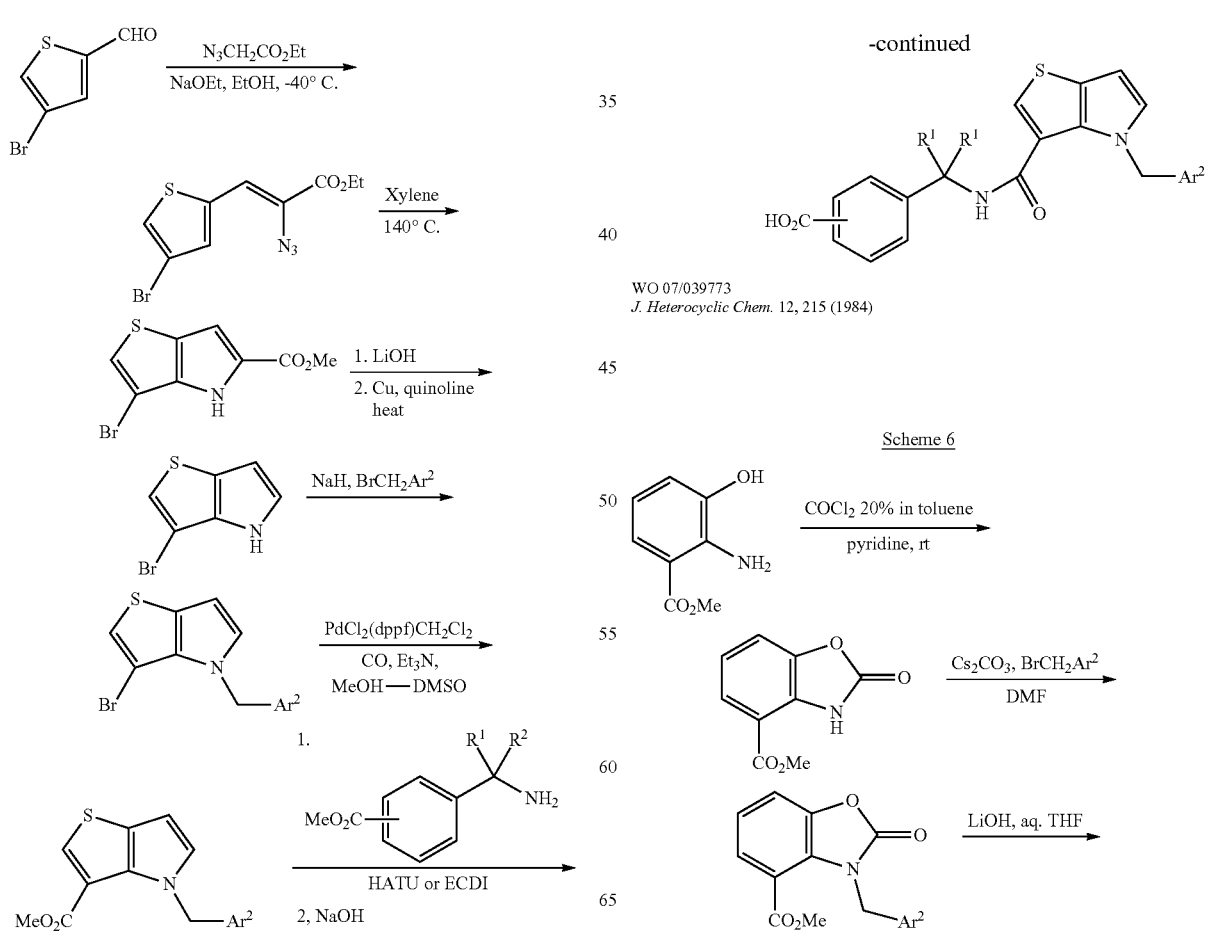
WO 07/039773
J. Heterocyclic Chem. 12, 215 (1984)

Scheme 8
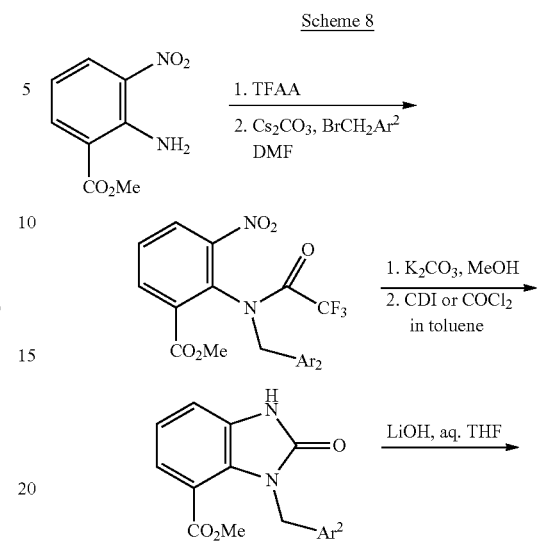
Scheme 7
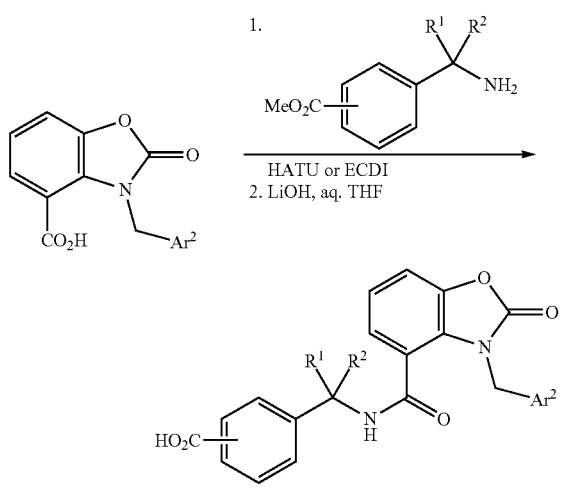
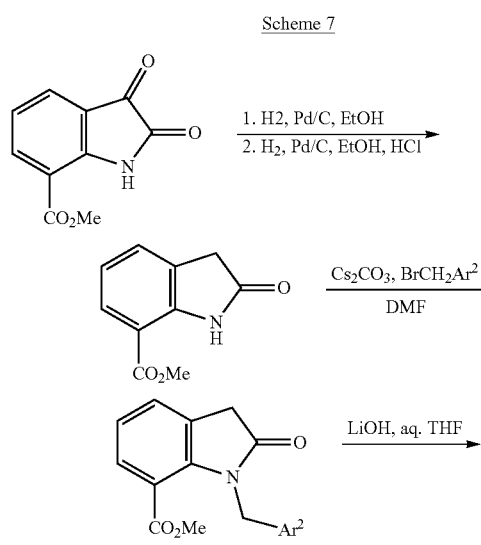
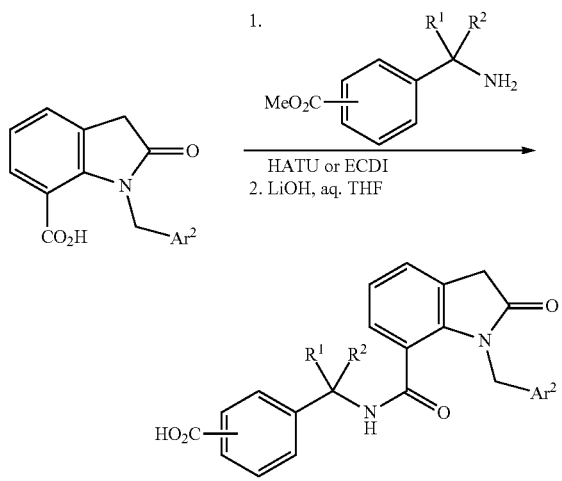
Scheme 9
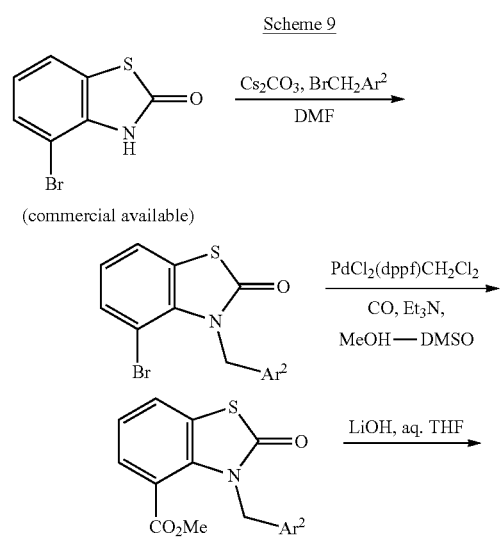

35
-continued
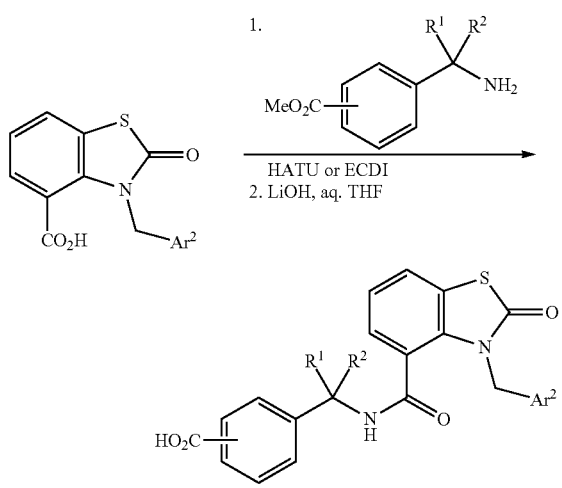
Scheme 10
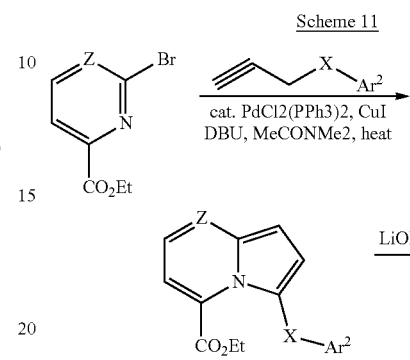
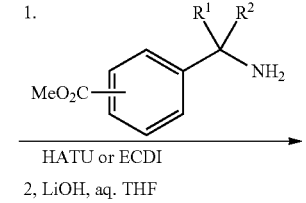
36
-continued
X = O, S
*Heterocycles*, 21, (2002)
Scheme 11
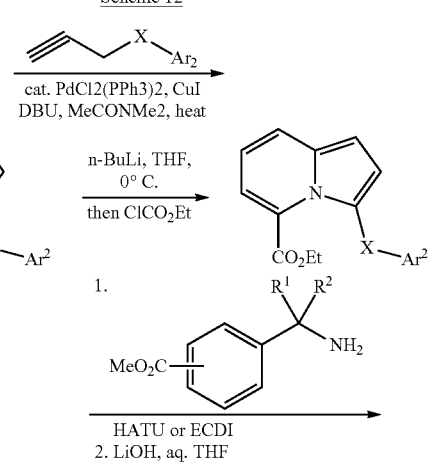
X = O, S, NH, NC$_{1-6}$alkyl
Z = CH, CC$_{1-6}$alkyl, N
CN 1948310A
Scheme 12

37

-continued

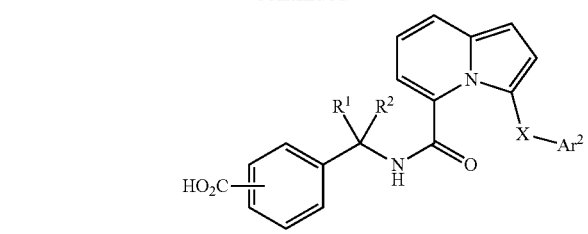

X = CH₂, O, S, NH, NC₁₋₆alkyl
Z = CH, CC₁₋₆alkyl, N

CN 1948310A & *J. Org. Chem.* 2054, (2005)

Scheme 13

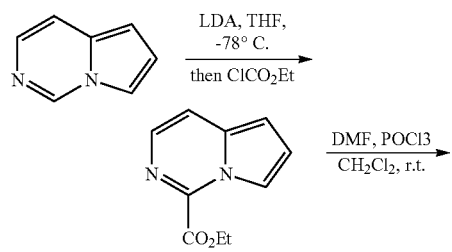

X = O, S
*J. Org. Chem.* 7788, (1999)

Scheme 14

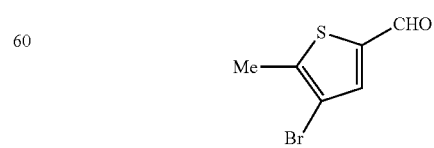

38

-continued

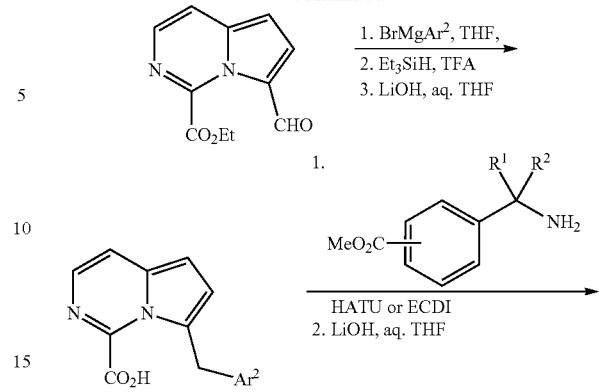

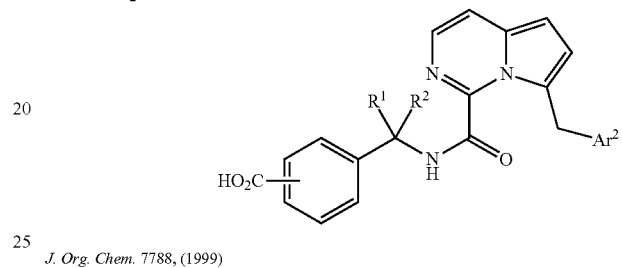

*J. Org. Chem.* 7788, (1999)

In the above schemes, the designation Ar2 corresponds to Ar2 in Formula I and is optionally substituted as described herein.

The following Examples are provided to further describe the invention and are not to be construed as limitations thereof.

Example 1

(S)-4-(1-{[2-Methyl-4-(4-trifluoromethyl-benzyl)-4H-thieno[3,2-b]pyrrole-3-carbonyl]-amino}-ethyl)-benzoic acid

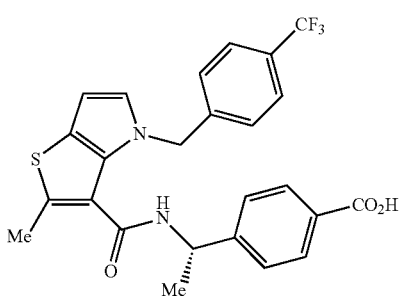 [SMILES: Cc1sc2ccn(Cc3ccc(C(F)(F)F)cc3)c2c1C(=O)N[C@@H](C)c1ccc(C(=O)O)cc1]

Step 1 4-Bromo-5-methyl-thiophene-2-carbaldehyde

The title compound was prepared according to the procedure described in J. Phys. Chem. Vol. 106, 1659 (2002). To a solution of 40 g of 2-methyl-2-carbaldehyde in 320 ml of AcOH was added a solution of bromine (20 ml) in 150 ml of AcOH over a period of 6 h. After reaction mixture was stirred for 20 h at room temperature, a solution 8 mL of bromine in 50 ml of AcOH was added and stirring was continued for another 24 h. The mixture was then concentrated under vacuum. The residue was treated with 300 ml of saturated aqueous solution of Na2CO3 and extracted with 2×500 ml of ether. The combined ether extracts was dried over Na2SO4, filtered and concentrated. The crude product was swished from 100 ml of 10:1 hexane/ether to give 40 g of the title compound.

1H NMR (500 MHz, acetone-$d_6$): δ 9.88 (s, 1H), 7.90 (s, 1H), 2.53 (s, 3H).

Step 2 2-azido-3-(4-bromo-5-methyl-thiophen-2-yl)-acrylic acid methyl ester

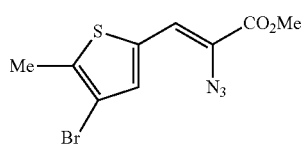 [SMILES: COC(=O)/C(=C/c1cc(Br)c(C)s1)N=[N+]=[N-]]

To a solution of azido-acetic acid methyl ester (25 g, 220 mmol) and 4-bromo-5-methyl-thiophene-2-carbaldehyde (15 g, 73 mmol) in 50 ml of MeOH cooled at −25° C. was added a solution NaOMe in MeOH (51 ml, 4.36 M). The resulting mixture (slush) was stirred with a mechanical stirrer for 2 h at 0° C. and the 200 g of ice was added. The yellow solid was collected by filtration and air-dried to give 18 g of the title product which was used for the next step without further purification.

Step 3 3-bromo-2-methyl-4H-thieno[3,2-b]pyrrole-5-carboxylic acid methyl ester

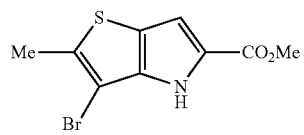 [SMILES: COC(=O)c1cc2sc(C)c(Br)c2[nH]1]

To a refluxing xylene (100 ml) was added the crude product of Step 2 (18 g) in 250 ml of xylene over a period of 20 min. After refluxing for 10 min, the reaction mixture was cooled and concentrated to volume of about 100 ml. The solid was collected by filtration to give 12.5 g of the title compound as a white solid.

1H NMR (500 MHz, acetone-$d_6$): δ 11.3 (bs, 1H), 7.14 (s, 1H), 3.85 (s, 3H), 2.47 (s, 3H).

Step 4 3-Bromo-2-methyl-4-(4-trifluoromethyl-benzyl)-4H-thieno[3,2-b]pyrrole-5-carboxylic acid methyl ester

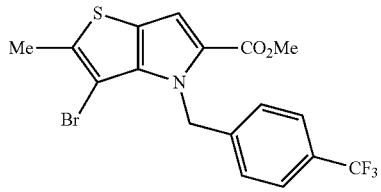 [SMILES: COC(=O)c1cc2sc(C)c(Br)c2n1Cc1ccc(C(F)(F)F)cc1]

A solution of 3-bromo-2-methyl-4H-thieno[3,2-b]pyrrole-5-carboxylic acid methyl ester (8.3 g), 4-trifluoromethybenzyl bromide (8.4 g) and Cs2CO3 (25 g) was stirred for 14 h at room temperature. The reaction mixture was then diluted with 200 ml of 1:1 hexane/EtOAc and filtered through a pad of silica gel. The filtrate was concentrated to give 15 g of the crude title compound which was used for the next step without further purification.

Step 4 3-Bromo-2-methyl-4-(4-trifluoromethyl-benzyl)-4H-thieno[3,2-b]pyrrole-5-carboxylic acid

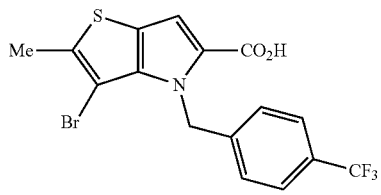 [SMILES: Cc1sc2cc(C(=O)O)n(Cc3ccc(C(F)(F)F)cc3)c2c1Br]

To a solution of the crude product of Step 3 (15 g) in 200 ml of 1:1 MeOH/THF was added 100 ml of 1N aqueous LiOH solution. The reaction mixture was stirred at 55° C. for 4 h and the concentrated under reduced pressure to move the volatile solvent. The resulting aqueous solution was treated with 20 ml of AcOH and stirred for 2 h. The solid was collected by filtration to give 11.5 of the title compound as a white powder.

1H NMR (500 MHz, acetone-$d_6$): δ 7.68 (d, 2H), 7.35 (s, 1H), 7.22 (d, 2H), 6.25 (s, 2H), 2.48 (s, 3H).

Step 5 3-Bromo-2-methyl-4-(4-tifluoromethyl-benzyl)-4H-thieno[3,2-b]pyrrole

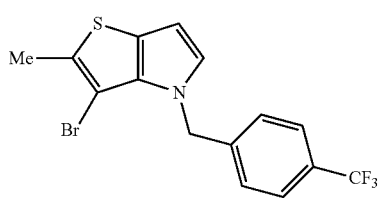 [SMILES: Cc1sc2ccn(Cc3ccc(C(F)(F)F)cc3)c2c1Br]

A mixture of 10 g of the product of Step 4 and 1 g of copper powder in 150 ml of quinoline was heated in oil bath at 140° C. for 4 h. The reaction mixture was cooled and acidified with 6 N HCl and then extracted with 500 ml of ether. The ether layer was washed with 200 ml of 2 N HCl, dried over Na2SO4, filtered, and concentrated to give 7 g of the title compound as a light brown solid.

1H NMR (500 MHz, acetone-$d_6$): δ 7.69 (d, 2H), 7.31 (d, 2H), 7.13 (d, 1H), 6.44 (d, 1H), 5.72 (s, 2H), 2.40 (s, 3H).

Step 6 2-Methyl-4-(4-trifluoromethyl-benzyl)-4H-thieno[3,2-b]pyrrole-3-carboxylic acid methyl ester

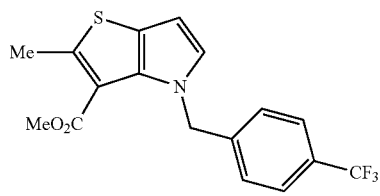 [SMILES: COC(=O)c1c(C)sc2ccn(Cc3ccc(C(F)(F)F)cc3)c12]

A mixture of 0.7 g of the product of Step 5, 0.7 g of PdCl2dppf.CH2Cl2, and 0.56 ml of Et3N in 30 ml of 2:1 DMSO/MeOH was heated under CO (balloon pressure) at 75° C. for 4 days. The reaction mixture was poured into 200 ml of 1:1 heaxan/EtOAc and stirred with 100 ml of water for 4 h. The organic layer was washed with 100 ml of brine and dried over Na2SO4, filtered, and concentrated. The residue was purified by silica gel chromatography eluted with a gradient up to 15% EtOAc/hexane to give 0.35 g of the title compound as a light brown solid.

1H NMR (500 MHz, acetone-$d_6$): δ 7.65 (d, 2H), 7.20 (d, 2H), 7.16 (d, 1H), 6.45 (d, 1H), 5.78 (s, 2H), 3.73 (s, 3H), 2.65 (s, 3H).

Step 7 2-Methyl-4-(4-trifluoromethyl-benzyl)-4H-thieno[3,2-b]pyrrole-3-carboxylic acid

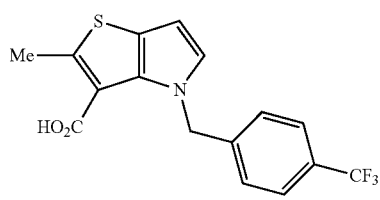 [SMILES: Cc1sc2ccn(Cc3ccc(C(F)(F)F)cc3)c2c1C(=O)O]

A mixture of 0.35 g of the product of Step 6 was dissolved in 15 ml THF, 10 ml of MeOH and 5 ml of water, followed by 5 ml of 1N aqueous LiOH solution. After stirring for 5 h at room temperature, 1 ml of AcOH was added and the mixture was extracted with 50 ml of EtOAc. The organic layer was washed with 25 ml of brine and dried over Na2SO4, filtered, and concentrated to give 0.30 g of the title compound as a white solid.

1H NMR (500 MHz, acetone-$d_6$): δ 11.25 (bs, 1H), 7.62 (d, 2H), 7.21 (d, 2H), 7.15 (d, 1H), 6.45 (d, 1H), 5.86 (s, 2H), 2.72 (s, 3H).

Step 8 (S)-4-(1-{[2-Methyl-4-(4-trifluoromethyl-benzyl)-4H-thieno[3,2-b]pyrrole-3-carbonyl]-amino}-ethyl)-benzoic acid

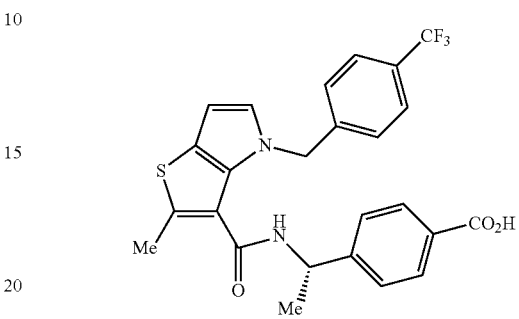

A mixture of 0.043 g of 2-methyl-4-(4-trifluoromethyl-benzyl)-4H-thieno[3,2-b]pyrrole-3-carboxylic acid, 0.060 g of (S)-4-(1-amino-ethyl)-benzoic acid methyl ester, 0.040 g of HOBT-hydrate, 0.054 g of ethyl-dimethylaminopropyl-carbodiimide hydrochloride (EDCI) and 0.060 ml of N-methylmorpholine in 2 ml of DMF was stirred at room temperature for 18 h. The reaction was then quenched with 1 ml of water and 2 ml of saturated NaHCO3 solution. The resulting mixture extracted with 15 ml of EtOAc. The organic layer was dried over Na2SO4, filtered, and concentrated to give the crude methyl ester which was dissolved in 2 ml THF, 2 mL MeOH and 0.5 mL water and treated with 0.5 mL of 1M LiOH solution. After stirring for 24 h at room temperature, the reaction mixture was concentrated under reduced pressure to remove THF and MeOH. The residue was diluted with 2 mL of water and treated with 0.3 mL of AcOH with vigorous stirring. After stirring for 2 h, the solid was collected by filtration and air-dried to give 0.029 g of the title compound as a white powder.

1H NMR (500 MHz, acetone-$d_6$): δ 7.99 (d, 2H), 7.82 (d, 1H), 7.54 (d, 2H), 7.52 (d, 2H), 7.16 (d, 2H), 7.10 (d, 2H), 6.40 (d, 1H), 5.50 (s, 2H), 5.24 (quintet, 1H), 2.54 (s, 3H), 1.52 (d, 3H).

Example 2

(S)-4-(1-{[4-(4-Trifluoromethyl-benzyl)-4H-thieno[3,2-b]pyrrole-3-carbonyl]-amino}-ethyl)-benzoic acid

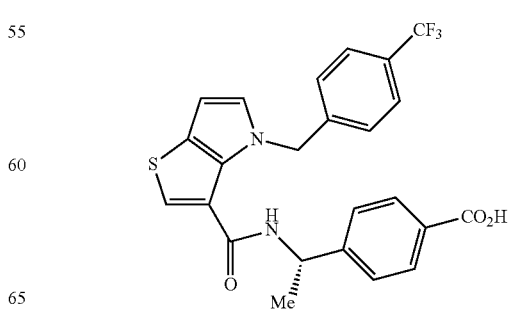

Step 1 2-Azido-3-(4-bromo-thiophen-2-yl)-acrylic acid methyl ester

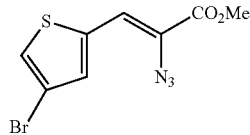 [SMILES: COC(=O)/C(=C/c1cc(Br)cs1)N=[N+]=[N-]]

To a solution of azido-acetic acid methyl ester (25 g, 220 mmol) and 15 g of 4-bromo-thiophene-2-carbaldehyde (14.0 g, 73 mmol) in 50 ml of MeOH cooled at −25° C. was added a solution NaOMe in MeOH (51 ml, 4.36 M). The resulting mixture (slush) was stirred with a mechanical stirrer for 2 h at 0° C. and the 200 g of ice was added. The yellow solid was collected by filtration and air-dried to give 15 g of the title product which was used for the next step without further purification.

Step 2 3-bromo-4H-thieno[3,2-b]pyrrole-5-carboxylic acid methyl ester

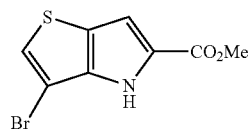

To a refluxing xylene (100 ml) was added the crude product of Step 2 (15 g) in 250 ml of xylene over a period of 20 min. After refluxing for 10 min, the reaction mixture was cooled and concentrated to volume of ~100 ml. The solid was collected by filtration to give 12 g of the title compound as a white solid.

1H NMR (500 MHz, acetone-$d_6$): δ 11.47 (bs, 1H), 7.52 (s, 1H), 7.22 (s, 1H), 3.87 (s, 3H).

Step 3 3-Bromo-4-(4-trifluoromethyl-benzyl)-4H-thieno[3,2-b]pyrrole-5-carboxylic acid methyl ester

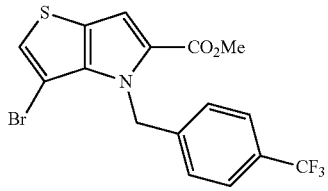 [SMILES: COC(=O)c1cc2scc(Br)c2n1Cc1ccc(C(F)(F)F)cc1]

A solution of 3-Bromo-4-(4-trifluoromethyl-benzyl)-4H-thieno[3,2-b]pyrrole-5-carboxylic acid methyl ester (2.3 g), 4-trifluoromethybenzyl bromide (2.4 g) and $Cs_2CO_3$ (4 g) was stirred for 14 h at room temperature. The reaction mixture was then diluted with 100 ml of 1:1 hexane/EtOAc and filtered through a pad of silica gel. The filtrate was concentrated to give 4.0 g of the crude title compound which was used for the next step without further purification.

Step 4 3-Bromo-4-(4-trifluoromethyl-benzyl)-4H-thieno[3,2-b]pyrrole-5-carboxylic acid

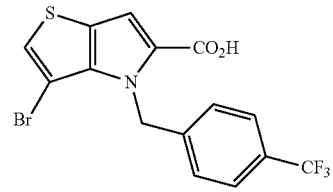

To a solution of the crude product of Step 3 (4 g) in 50 ml of 1:1 MeOH/THF was added 25 ml of 1N aqueous LiOH solution. The reaction mixture was stirred at 55° C. for 4 h and the concentrated under reduced pressure to move the volatile solvent. The resulting aqueous solution was treated with 5 ml of AcOH and stirred for 2 h. The solid was collected by filtration to give 3.2 of the title compound as a white powder.

1H NMR (500 MHz, acetone-$d_6$): δ 7.68 (d, 2H), 7.60 (s, 1H), 7.42 (s, 1H), 7.23 (d, 2H), 6.27 (s, 2H).

Step 5 3-Bromo-4-(4-trifluoromethyl-benzyl)-4H-thieno[3,2-b]pyrrole

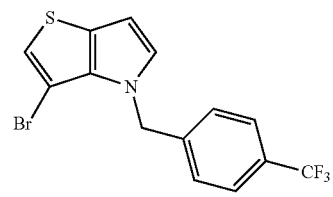 [SMILES: FC(F)(F)c1ccc(Cn2ccc3scc(Br)c32)cc1]

A mixture of 3 g of the product of Step 4 and 0.3 g of copper powder in 50 ml of quinoline was heated in oil bath at 140° C. for 4 h. The reaction mixture was cooled and acidified with 6 N HCl and then extracted with 150 ml of ether. The ether layer was washed with 200 ml of 2 N HCl, dried over Na2SO4, filtered, and concentrated to give 2.2 g of the title compound as a light brown solid.

1H NMR (500 MHz, acetone-$d_6$): δ 7.70 (d, 2H), 7.33 (d, 2H), 7.25 (d, 1H), 7.20 (s, 1H), 6.53 (d, 1H), 5.72 (s, 2H).

Step 6 4-(4-Trifluoromethyl-benzyl)-4H-thieno[3,2-b]pyrrole-3-carboxylic acid methyl ester

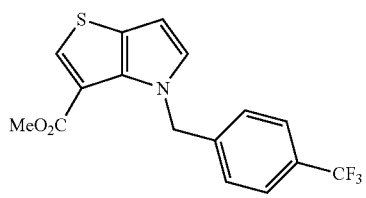 [SMILES: COC(=O)c1csc2ccn(Cc3ccc(C(F)(F)F)cc3)c12]

A mixture of 2.0 g of the product of Step 5, 0.54 g of $PdCl_2dppf.CH_2Cl_2$, and 1.8 ml of Et3N in 60 ml of 2:1 DMSO/MeOH was heated under CO (balloon pressure) at 75° C. for 24 h. The reaction mixture was poured into 400 ml of 1:1 heaxan/EtOAc and stirred with 200 ml of water for 4 h. The organic layer was washed with 100 ml of brine and dried over $Na_2SO_4$, filtered, and concentrated. The residue was purified by silica gel chromatography eluted with a gradient up to 15% EtOAc/hexane to give 1.7 g of the title compound as a light brown solid.

1H NMR (500 MHz, acetone-$d_6$): δ 8.06 (s, 1H), 7.63 (d, 2H), 7.27 (d, 2H), 7.23 (d, 1H), 6.57 (d, 1H), 5.95 (s, 2H), 3.78 (s, 3H).

Step 7 4-(4-Trifluoromethyl-benzyl)-4H-thieno[3,2-b]pyrrole-3-carboxylic acid

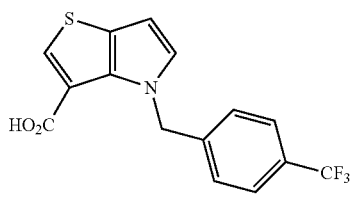 [SMILES: O=C(O)c1csc2ccn(Cc3ccc(C(F)(F)F)cc3)c12]

A mixture of 1.0 g of the product of Step 6 was dissolved in 45 ml THF, 30 ml of MeOH and 15 ml of water, followed by 15 ml of 1N aqueous LiOH solution. After stirring for 5 h at room temperature, 2 ml of AcOH was added and the mixture was extracted with 150 ml of EtOAc. The organic layer was washed with 50 ml of brine and dried over $Na_2SO_4$, filtered, and concentrated to give 0.9 g of the title compound as a white solid.

1H NMR (500 MHz, acetone-$d_6$): δ 11.10 (bs, 1H), 8.11 (s, 1H), 7.62 (d, 2H), 7.27 (d, 2H), 7.22 (d, 1H), 6.55 (s, 1H), 5.98 (s, 2H).

Step 8 (S)-4-(1-{[4-(4-Trifluoromethyl-benzyl)-4H-thieno[3,2-b]pyrrole-3-carbonyl]-amino}-ethyl)-benzoic acid

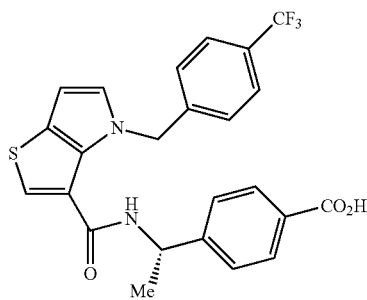 [SMILES: C[C@H](NC(=O)c1csc2ccn(Cc3ccc(C(F)(F)F)cc3)c12)c1ccc(C(=O)O)cc1]

A mixture of 0.107 g of 2-methyl-4-(4-trifluoromethyl-benzyl)-4H-thieno[3,2-b]pyrrole-3-carboxylic acid, 0.150 g of (S)-4-(1-amino-ethyl)-benzoic acid methyl ester, 0.100 g of HOBT-hydrate, 0.133 g of ethyl-dimethylaminopropyl-carbodiimide hydrochloride (EDCI) and 0.150 ml of N-methylmorpholine in 4 ml of DMF was stirred at room temperature for 18 h. The reaction was then quenched with 2 ml of water and 5 ml of sat. $NaHCO_3$ solution. The resulting mixture extracted with 20 ml of EtOAc. The organic layer was dried over $Na_2SO_4$, filtered, and concentrated to give the crude methyl ester which was dissolved in 4 ml THF, 4 mL MeOH and 1 mL water and treated with 1 mL of 1N LiOH solution. After stirring for 24 h at room temperature, the reaction mixture was concentrated under reduced pressure to remove THF and MeOH. The residue was diluted with 4 mL of water and treated with 0.7 mL of AcOH with vigorous stirring. After stirring for 2 h, the solid was collected by filtration and air-dried to give 0.110 g of the title compound as a white powder.

1H NMR (500 MHz, acetone-$d_6$): δ 8.05 (d, 1H), 8.01 (d, 2H), 7.74 (s, 1H), 7.54 (d, 2H), 7.51 (d, 2H), 7.26 (d, 1H), 7.20 (d, 2H), 6.50 (d, 1H), 5.83 (d, 1H), 5.72 (d, 1H), 5.27 (quintet, 1H), 1.51 (d, 3H).

Example 3

4-(1-{[2-Methyl-4-(4-trifluoromethyl-benzyl)-4H-thieno[3,2-b]pyrrole-3-carbonyl]amino}-cyclopropyl)-benzoic acid

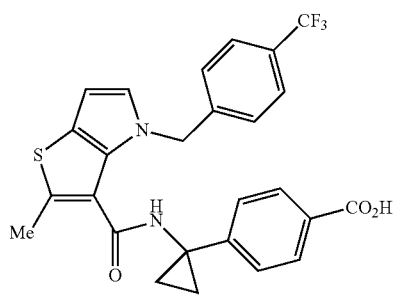 [SMILES: Cc1sc2ccn(Cc3ccc(C(F)(F)F)cc3)c2c1C(=O)NC1(c2ccc(C(=O)O)cc2)CC1]

A mixture of 0.3 g of 2-methyl-4-(4-trifluoromethyl-benzyl)-4H-thieno[3,2-b]pyrrole-3-carboxylic acid, 0.25 g of 4-(1-amino-cyclopropyl)-benzoic acid methyl ester, 0.5 g of HATU and 0.25 ml of $Pr_2NEt$ in 8 ml of DMF was stirred at room temperature for 16 h. The reaction was then diluted with 30 ml of water and extracted with 100 ml of EtOAc. The organic layer was washed with 50 ml of water and 50 ml of brine and dried over $Na_2SO_4$. The extract was filtered, and concentrated to give the crude methyl ester which was dissolved in 20 ml of 1:1 THF/MeOH and treated with 10 ml of 0.5 M aqueous LiOH solution. After stirring for 15 h at room temperature, 1 ml of AcOH was added and the reaction mixture was extracted with 75 ml of EtOAc. The organic layer was washed with 50 ml of brine, dried over $Na_2SO_4$. The extract was filtered and concentrated to give 0.25 g of the title compound as a light brown solid.

1H NMR (500 MHz, acetone-$d_6$): δ 11.12 (bs, 1H), 8.17 (s, 1H), 7.85 (d, 2H), 7.57 (d, 2H), 7.35 (d, 2H), 7.11 (d, 2H), 7.05 (d, 1H), 6.42 (d, 1H), 5.58 (s, 2H), 2.62 (s, 3H), 1.31 (m, 2H), 1.20 (m, 2H).

Example 4

4-(1-{[4-(4-Trifluoromethyl-benzyl)-4H-thieno[3,2-b]pyrrole-3-carbonyl]-amino}-cyclopropyl)-benzoic acid

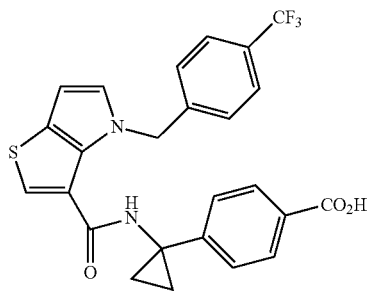 [SMILES: O=C(O)c1ccc(C2(NC(=O)c3csc4ccn(Cc5ccc(C(F)(F)F)cc5)c34)CC2)cc1]

A mixture of 0.33 g of 4-(4-Trifluoromethyl-benzyl)-4H-thieno[3,2-b]pyrrole-3-carboxylic acid, 0.23 g of 4-(1-amino-cyclopropyl)-benzoic acid methyl ester, 0.5 g of HATU and 0.25 ml of $Pr_2NEt$ in 8 ml of DMF was stirred at room temperature for 16 h. The reaction was then diluted with 30 ml of water and extracted with 100 ml of EtOAc. The organic layer was washed with 50 ml of water and 50 ml of brine and dried over Na2SO4. The extract was filtered, and concentrated to give the crude methyl ester which was dissolved in 20 ml of 1:1 THF/MeOH and treated with 10 ml of 0.5 N aqueous LiOH solution. After stirring for 15 h at room temperature, 1 ml of AcOH was added and the reaction mixture was extracted with 75 ml of EtOAc. The organic layer was washed with 50 ml of brine, dried over $Na_2SO_4$. The extract was filtered and concentrated to give 0.22 g of the title compound as a light brown solid.

1H NMR (500 MHz, acetone-$d_6$): δ 11.03 (bs, 1H), 8.49 (s, 1H), 7.40 (d, 2H), 7.83 (s, 1H), 7.57 (d, 2H), 7.32 (d, 2H), 7.23 (d, 1H), 7.19 (d, 2H), 6.51 (d, 1H), 5.35 (s, 2H), 1.35 (m, 2H), 1.32 (m, 2H).

Example 5

4-(1-{[2-Oxo-1-(4-trifluoromethyl-benzyl)-2,3-dihydro-1H-indole-7-carbonyl]-amino}-cyclopropyl)-benzoic acid

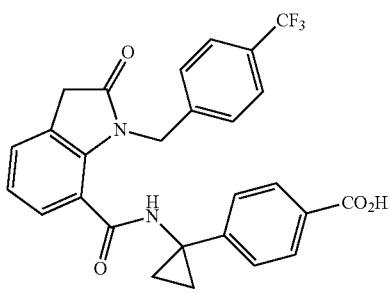 [SMILES: O=C(O)c1ccc(C2(NC(=O)c3cccc4c3N(Cc3ccc(C(F)(F)F)cc3)C(=O)C4)CC2)cc1]

Step 1 7-Bromo-1-(4-trifluoromethylbenzyl)-1,3-dihydro-indol-2-one

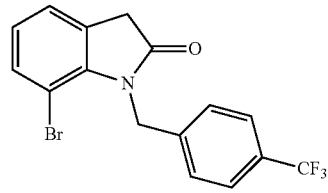 [SMILES: O=C1Cc2cccc(Br)c2N1Cc1ccc(C(F)(F)F)cc1]

A mixture of 7-bromo-1H-indole-2,3-dione (4.5 g), $Cs_2CO_3$ (10 g) and 1-bromomethyl-4-trifluoromethylbenzene (5 g) in 50 ml of DMF was stirred at 55° C. for 6 h. The reaction mixture was cooled to r.t., diluted with 100 ml of 1:1 hexane/EtOAc and filtered through a pad of silica gel. The filtrate was concentrated under vacuum and the crude product was dissolved in 100 ml of ethanol and 10 ml of 50% aqueous solution of hydrazine. The resulting mixture was heated to reflux for 10 h and diluted with 50 ml of water. After cooling to r.t., solid was collected by filtration and air-dried to give the title compound as a white solid (5.2 g).

1H NMR (500 MHz, acetone-$d_6$): δ 7.68 (d, 2H), 7.50 (d, 2H), 7.35-7.40 (m, 2H), 6.97 (t, 1H), 5.48 (s, 2H), 3.76 (s, 2H).

Step 2 2-Oxo-1-(4-trifluoromethyl-benzyl)-2,3-dihydro-1H-indole-7-carboxylic acid

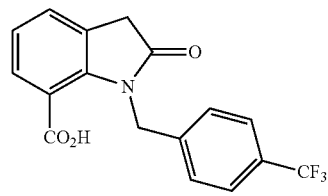 [SMILES: O=C(O)c1cccc2c1N(Cc1ccc(C(F)(F)F)cc1)C(=O)C2]

A mixture 2.8 g of 7-bromo-1-(4-trifluoromethylbenzyl)-1,3-dihydro-indol-2-one, 0.70 g of $PdCl_2dppf.CH_2Cl_2$, and 2.34 ml of Et3N in 75 ml of 2:1 DMSO/MeOH was heated under CO (balloon pressure) at 75° C. for 24 h. The reaction mixture was poured into 400 ml of 1:1 heaxan/EtOAc and stirred with 200 ml of water for 4 h. The organic layer was washed with 150 ml of brine and dried over $Na_2SO_4$, filtered through a pad of silica gel, and concentrated. The residue was dissolved in 60 ml THF, 20 ml of MeOH and 20 ml of water, followed by 30 ml of 1N aqueous LiOH solution. After stirring for 5 h at room temperature, 5 ml of AcOH was added and the mixture was extracted with 250 ml of EtOAc. The organic layer was washed with 50 ml of brine and dried over $Na_2SO_4$, filtered, and concentrated. The residue was swished from 50 ml of 1:1 hexane/EtOAc to give 1.2 g of the title compound as a light brown solid.

1H NMR (500 MHz, acetone-d$_6$): δ 11.3 (bs, 1H), 7.58 (d, 2H), 7.52 (d, 1H), 7.50 (d, 1H), 7.33 (d, 2H), 7.08 (t, 1H), 5.40 (s, 2H), 3.76 (s, 2H).

Step 3 4-(1-{[2-Oxo-1-(4-trifluoromethylbenzyl)-2, 3-dihydro-1H-indole-7-carbonyl]-amino}-cyclopropyl)-benzoic acid

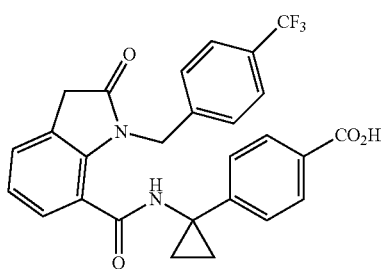 [SMILES: O=C(O)c1ccc(C2(NC(=O)c3cccc4c3N(Cc3ccc(C(F)(F)F)cc3)C(=O)C4)CC2)cc1]

A mixture of 0.40 g of 2-oxo-1-(4-trifluoromethyl-benzyl)-2,3-dihydro-1H-indole-7-carboxylic acid, 0.29 g of (±)4-(1-amino-ethyl)-benzoic acid methyl ester, 0.19 g of HOBT-hydrate, 0.30 g of ethyl-dimethylaminopropyl-carbodiimide hydrochloride (EDC1) and 0.150 ml of N-methyl-morpholine in 7 ml of DMF was stirred at room temperature for 16 h. The reaction was then quenched with 10 ml of water and 5 ml of sat. NaHCO$_3$ solution. The resulting mixture extracted with 25 ml of EtOAc. The organic layer was dried over Na$_2$SO$_4$, filtered, and concentrated to give the crude methyl ester (0.3 g) which was dissolved in 5 ml THF, 5 mL MeOH and treated with 4 mL of 1N LiOH solution. After stirring at 50° C. for 12 h, the reaction mixture was concentrated under reduced pressure to remove THF and MeOH. The residue was diluted with 8 mL of water and treated with 1 mL of AcOH with vigorous stirring. After stirring for 2 h, the solid was collected by filtration and air-dried to give 0.25 g of the title compound as a white powder.

1H NMR (500 MHz, DMSO-d$_6$): δ 12.80 (bs, 1H), 9.18 (s, 1H), 7.78 (d, 2H), 7.61 (d, 2H), 7.46 (d, 1H), 7.39 (d, 1H), 7.23 (d, 2H), 7.20 (d, 2H), 7.14 (t, 1H), 5.40 (s, 2H), 3.73 (s, 2H), 1.10 (m, 2H), 0.73 (m, 2H).

What is claimed is:

1. A compound of Formula I

Formula I

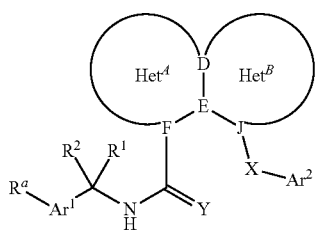

or a pharmaceutically acceptable salt thereof, wherein:
R$^1$, R$^2$ are independently selected from the group consisting of: hydrogen, C$_{1-6}$alkyl, C$_{1-6}$ cyclolkyl, C$_{1-6}$fluorocycloalkyl, and C$_{1-6}$fluoroalkyl; or R$^1$, R$^2$, together with the carbon atom to which they are both attached, complete a three- to six-membered carbocyclic ring which is optionally substituted with R$^c$, or complete a three- to six-membered ring which contains one or two heteroatom(s) each independently selected from S, O or NR$^b$, wherein R$^b$ is selected from the group consisting of: hydrogen, C$_{1-6}$alkyl, C$_{1-6}$cyclolkyl, C$_{1-6}$fluorocycloalkyl, C$_{1-6}$ fluoroalkyl, aryl, heteroaryl, C(O)C$_{1-6}$alkyl, C(O)aryl, S(O)$_2$alkyl, and S(O)$_2$aryl;

Y is O or S;

X is a bond, =CH—, CH$_2$, O, or S;

Ar$^1$ and Ar$^2$ are independently aryl, wherein Ar$^1$ and Ar$^2$ are optionally substituted with one to three R$^c$ groups;

R$^c$ is independently halo or R$^1$,

R$^a$ is —CO$_2$H, —CO$_2$M, —C(O)NHS(O)$_2$R$^{aa}$ or

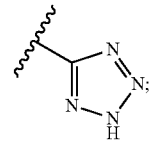 [SMILES: *c1nn[nH]n1]

R$^{aa}$ is C$_{1-6}$alkyl, C$_{1-6}$haloalkyl, C$_{1-6}$cycloalkyl, C$_{1-6}$cyclohaloalkyl, aryl, or heteroaryl;

M is a pharmaceutically acceptable salt or an ester prodrug group;

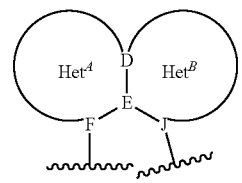

has the structure

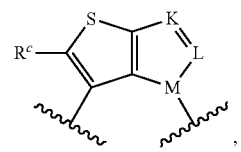

wherein —K-L-M- is —C(R$^3$)=C(R$^4$)—N—, R$^3$ is hydrogen, and R$^4$ is hydrogen.

2. The compound according to claim 1, or pharmaceutically acceptable salt thereof, having the Formula Ia Formula Ia

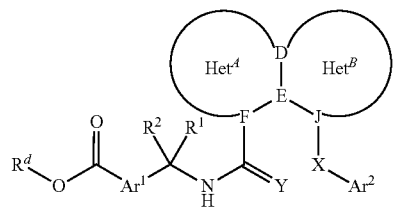

wherein R$^d$ represents a C$_1$-C$_{10}$ alkyl, a C$_7$-C$_{12}$ aralkyl, aryl, or heteroaryl.

3. The compound according to claim 1, or pharmaceutically acceptable salt thereof, in the form of a nitric oxide releasing ester prodrug of Formula Ib Formula Ib

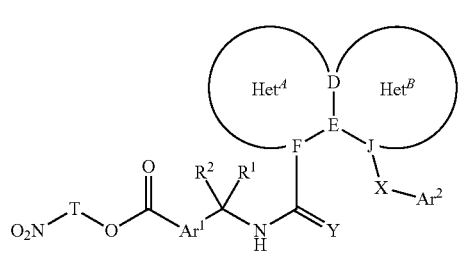

wherein T is a suitable linker.

4. The compound according to claim 1, or pharmaceutically acceptable salt thereof, in the form of a nitric oxide releasing ester prodrug of Formula Ic Formula Ic

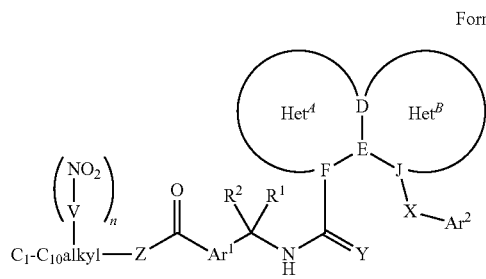

wherein

Z is O, S or $NR^e$, $R^e$ is hydrogen, alkyl or aryl;

each V is independently selected from the group consisting of O and S, and is independently attached to any one carbon atom of the $C_1$-$C_{10}$alkyl; and n is 1, 2, 3 or 4.

5. The compound according to claim 1, or pharmaceutically acceptable salt thereof, in the form of a nitric oxide releasing prodrug of Formula Id Formula Id

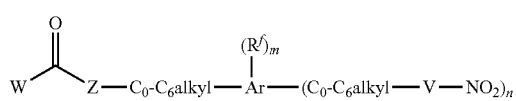

wherein:

Z is O, S or $NR^e$, $R^e$ is hydrogen, alkyl or aryl;

each V is selected from the group consisting of O and S, and is independently attached to any one carbon atom of the alkyl;

$R^f$ is selected from the group consisting of:
(a) hydrogen,
(b) halo,
(c) alkoxy,
(d) alkylthio,
(e) CN,
(f) $CF_3$,
(g) alkyl,
(h) alkylsulfonyl
(i) $S(O)_2NH_2$, and
(j) $S(O)_2NH$-alkyl;

W is

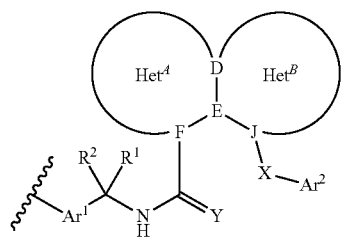

6. The compound according to claim 2 having the Formula Ie, or a pharmaceutically acceptable salt thereof Formula Ie wherein n is an integer from 1 to 10.

7. The compound according to claim 3 having the Formula If or a pharmaceutically acceptable salt thereof Formula If wherein n and m are each independently an integer from 1 to 10.

8. The compound according to claim 4 having the Formula Ig, or a pharmaceutically acceptable salt thereof Formula Ig

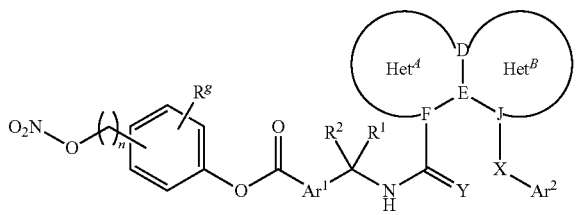

wherein n is an integer of 1 to 6;

$R^g$ is H, halogen, alkyl, or haloalkyl.

9. The compound according to claim 1 of Formula Ih, or a pharmaceutically acceptable salt thereof Formula Ih

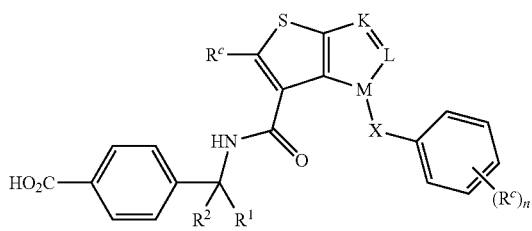

wherein R¹, R² and R$^c$ are defined as in claim 1;
n is 1, 2, 3, or 4;
X is a bond, —CH$_2$—, or —CHR¹.

10. The compound according to claim 1 of Formula Il, or a pharmaceutically acceptable salt thereof Formula Il wherein R$^c$ is defined as in claim 1;

R$^{cc}$ is hydrogen, C$_{1-6}$alkyl, or C$_{1-6}$cycloalkyl.

11. The compound according to claim 1, selected from the group consisting of:
- 4-((1S)-1-{[4-(4-Chlorobenzyl)-4H-thieno[3,2-b]pyrrole-3-carbonyl]amino}ethyl)benzoic acid;
- 4-((1S)-1-{[4-(4-Chlorobenzyl)-2-methyl-4H-thieno[3,2-b]pyrrole-3-carbonyl]amino}ethyl)benzoic acid;
- 4-((1S)-1-{[4-(4-trifluoromethylbenzyl)-2-methyl-4H-thieno[3,2-b]pyrrole-3-carbonyl]amino}ethyl)benzoic acid;
- 4-(1-{[4-(4-Chloro-benzyl)-2-methyl-4H-thieno[3,2-b]pyrrole-3-carbonyl]amino}cyclopropyl)benzoic acid;
- 4-(1-{[2-Methyl-4-(4-trifluoromethyl-benzyl)-4H-thieno[3,2-b]pyrrole-3-carbonyl]amino}cyclopropyl)benzoic acid;
- 4-(1-{[5-Oxo-4-(4-trifluoromethylbenzyl)-5,6-dihydro-4H-thieno[3,2-b]pyrrole-3-carbonyl]amino}cyclopropyl)benzoic acid; and
- 4-(1-Methyl-1-{[4-(4-trifluoromethylbenzyl)-4H-thieno[3,2-b]pyrrole-3-carbonyl]amino}ethyl)benzoic acid;

or a pharmaceutically acceptable salt thereof.

12. The compound of claim 11, wherein the compound is an ester prodrug.

13. A pharmaceutical composition comprising a compound of Formula I, or a pharmaceutically acceptable salt thereof, in admixture with one or more physiologically acceptable carriers or excipients.

14. The compound of claim 12, wherein the compound is a nitric oxide releasing ester prodrug.

\* \* \* \* \*